United States Patent
Rault et al.

[11] Patent Number: 5,627,203
[45] Date of Patent: May 6, 1997

[54] TRICYCLIC OXIME ETHERS

[75] Inventors: Sylvain Rault, Moult; Max Robba, Paris; Jean-Charles Lancelot, Le Bourg; Hervé Prunier, Caen; Pierre Renard, Versailles; Bruno Pfeiffer, Eaubonne; Béatrice Guardiola-Lemaitre, Saint-Cloud; Marie-Claire Rettori, Courbevoie, all of France

[73] Assignee: Adir et Compagnie, Courbevoie, France

[21] Appl. No.: 576,678

[22] Filed: Dec. 21, 1995

[30] Foreign Application Priority Data

Dec. 22, 1994 [FR] France .................................. 94 15431

[51] Int. Cl.$^6$ .......................... A61K 31/40; C07D 513/14
[52] U.S. Cl. .......................... 514/411; 514/321; 546/192; 548/428
[58] Field of Search .......................... 514/321, 411; 546/192; 548/428

[56] References Cited

U.S. PATENT DOCUMENTS

| | | | |
|---|---|---|---|
| 3,903,164 | 9/1975 | Goransson-Dahlander | 564/257 X |
| 4,308,399 | 12/1981 | Takacs et al. | 564/257 |
| 4,395,413 | 7/1983 | Budai et al. | 564/257 X |

OTHER PUBLICATIONS

Kilpatrick, Gavin J., et al., *5-HT$_3$ Receptors*, Medicinal Research Reviews, vol. 10, No. 4, 441–475 (1990).

Hoyer, Danies, et al., *VII. International Union of Pharmacology Classification of Receptors for 5-Hydroxytryptamine (Serotonin)*, Pharmacology Reviews, vol. 46, No. 2, 157–203 (1994).

Langer, S.Z., et al., *Inhibitors of Serotonin Uptake*, in Serotonin from Cell Biology to Pharmacology and Therapeutics, (P.M. Vanhoutte, et al. eds.) 197–205 (1993 Kluwer Academic Publishers).

Primary Examiner—Jacqueline Haley
Attorney, Agent, or Firm—The Firm of Gordon W. Hueschen

[57] ABSTRACT

The present invention relates to compounds of formula (I):

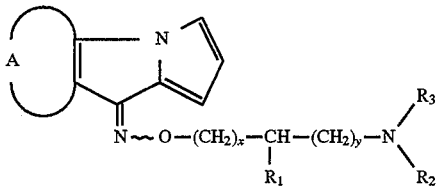

wherein A, x, y, $R_1$, $R_2$ and $R_3$ are as defined in the description. The compounds are useful for treating diseases requiring a selective serotonin reuptake site and 5-HT$_{2c}$ or 5-HT$_3$ ligand.

11 Claims, No Drawings

TRICYCLIC OXIME ETHERS

The present invention relates to new tricyclic oxime ethers, to processes for their preparation and to pharmaceutical compositions containing them.

Some examples of mono- or poly-cyclic oxime ethers are known from the literature. Of those sources, especially the patents BAYER EP 544 168 and EP 544 169 may be mentioned, which claim oxime ethers corresponding to the following general formulae:

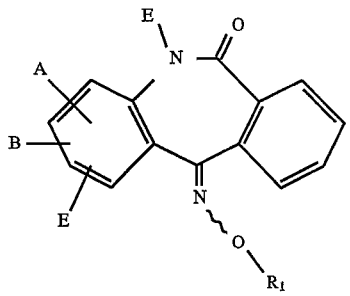

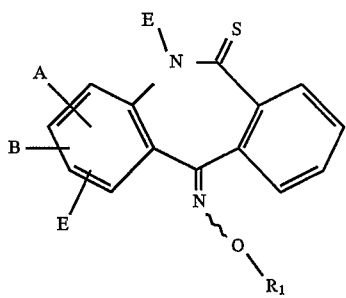

Those compounds are described as being reverse transcriptase inhibitors that can be used in the treatment of retrovirus disorders such as AIDS.

The Applicant has discovered new oxime ethers having a completely original tricyclic structure which are unexpectedly characterised by a very strong affinity for $5HT_{2C}$ and/or $5HT_3$ receptors and also for serotonin reuptake sites. That high affinity is associated with a prominent selectivity with vis à vis other serotoninergic receptors.

The potential and the therapeutic value of compounds that bind strongly to $5HT_{2C}$ and/or $5HT_3$ receptors are well known and in that connection the following reviews may usefully be referred to:

G. J. KILPATRICK "$5HT_3$ receptors" (Medicinal Research Reviews, 1990, 10(4), p 441–475).

D. HOYER et al "VII International Union of Pharmacology Classification of Receptor for 5-hydroxytryptamine (Serotonin)" (Pharmacological Reviews, 1994, 46 (2) pp 157–203).

The same applies in respect of compounds that inhibit the reuptake of serotonin; see in that connection the review by S. Z. LANGER and D. GRAHAM entitled "Inhibitors of serotonin uptake" taken from the work "SEROTONIN from cell biology to pharmacology and therapeutics" (P. M. VANHOUTTE et al. (eds.) 1993 Klurver Academic Publisher, the Netherlands).

The value of the compounds of the present invention is all the greater since they act powerfully and simultaneously at those different sites of action, rendering them very valuable therapeutically.

The invention relates more especially to compounds of formula (I):

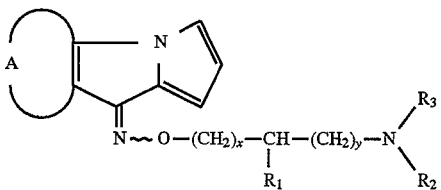

wherein $R_1$ is selected from:
 hydrogen,
 alkyl,
 alkenyl,
 cycloalkyl,
 cycloalkylalkyl of which the straight or branched alkyl chain has from 1 to 4 carbon atoms,
 hydroxy,
 alkoxy,
 optionally substituted phenyl,
 optionally substituted phenylalkyl of which the straight or branched alkyl chain has from 1 to 4 carbon atoms,
 optionally substituted phenoxy, and
 optionally substituted phenylalkoxy of which the straight or branched alkyl chain has from 1 to 4 carbon atoms,
 or $R_1$ forms with $R_2$ and the chain

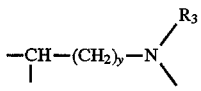

carrying them a nitrogen-containing ring system having from 5 to 8 ring members, $R_2$ and $R_3$ are each selected, independently of the other, from:
 hydrogen,
 alkyl,
 alkenyl,
 cycloalkyl,
 optionally substituted indanyl,
 cycloalkylalkyl of which the straight or branched alkyl chain has from 1 to 4 carbon atoms,
 optionally substituted phenyl, and
 optionally substituted phenylalkyl of which the straight or branched alkyl chain has from 1 to 4 carbon atoms,
 or $R_2$ and $R_3$ form together with the nitrogen atom carrying them a heterocyclic system selected from:

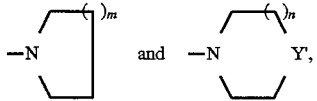

wherein:
 m is an integer of which the value may be 0, 1, 2, 3, or 4,
 n is an integer of which the value may be 0, 1, or 2,
 Y' is selected from oxygen, sulfur and the group

$R_4$ being selected from:
hydrogen,
alkyl, and
optionally substituted —$(CH_2)_\sigma$-phenyl, wherein $\sigma$ is an integer of which the value may be 0, 1, 2, 3, or 4, x and y represent identical or different integers of which the values may each, independently of the other, be 0, 1, 2, 3, or 4, A represents:

a group of formula ($\alpha$):

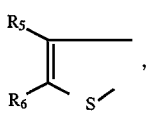

and thus forms with the heterocyclic system carrying it a thieno[2,3-d]pyrrolo[1,2-a]pyrrole of the general formula ($I_\alpha$):

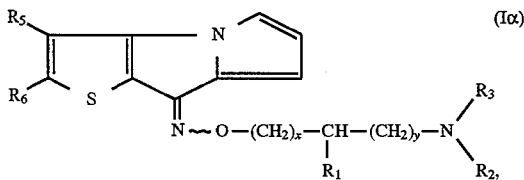

wherein $R_1$, $R_2$, $R_3$, x, and y are as defined hereinbefore and $R_5$ and $R_6$, which are identical or different, each represents, independently of the other, a group selected from:
hydrogen,
alkyl,
hydroxy,
alkoxy,
halogen,
trifluoromethyl,
alkoxycarbonyl,
optionally substituted —$(CH_2)_p$-phenyl wherein p is an integer of which the value may be 0, 1, 2, 3, or 4, and
optionally substituted —O—$(CH_2)_{p'}$-phenyl wherein p' is an integer of which the value may be 0, 1, 2, 3, or 4, a group of formula ($\beta$):

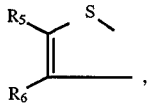

and thus forms with the heterocyclic system carrying it a thieno[3,2-d]pyrrolo[1,2-a]pyrrole of the general formula ($I_\beta$):

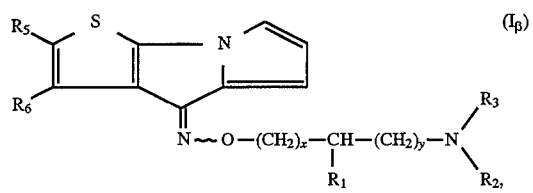

wherein $R_1$, $R_2$, $R_3$, $R_5$, $R_6$, x and y are as defined hereinbefore, a group of formula ($\gamma$):

and thus forms with the heterocyclic system carrying it a pyrrolo[1,2-a]indole of the general formula ($I_\gamma$):

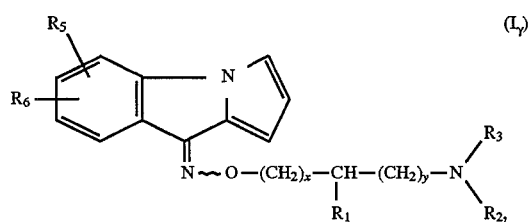

wherein $R_1$, $R_2$, $R_3$, $R_5$, $R_6$, x and y are as defined hereinbefore,
their cis or trans isomers in respect of the oxime ether, their enantiomers or diastereoisomers, and
their hydrates and/or pharmaceutically-acceptable addition salts with an acid or a base,
it being understood, unless specified otherwise, that:
the terms "alkyl" and "alkoxy" represent straight-chain or branched groups having from 1 to 6 carbon atoms,
the term "alkenyl" represents a straight-chain or branched unsaturated carbon-containing group having from 2 to 6 carbon atoms,
the term "cycloalkyl" represents a carbon ring system having from 3 to 8 ring members,
the expressions "optionally substituted indanyl", "optionally substituted phenyl", "optionally substituted phenoxy", "optionally substituted phenylalkyl", "optionally substituted —$(CH_2)_\sigma$-phenyl", "optionally substituted —$(CH_2)_p$-phenyl", optionally substituted "—O—$(CH_2)_{p'}$-phenyl" and "optionally substituted phenylalkoxy" denote that the phenyl radical may optionally be substituted by one or more identical or different substituents selected from alkyl, alkoxy, hydroxy, halogen, trifluoromethyl, nitrile and nitro.

Among the acids that may be used to form a pharmaceutically-acceptable addition salt with the compounds of the invention there may be mentioned by way of example, and in a non-limiting manner, hydrochloric, sulfuric, phosphoric, tartaric, malic, maleic, succinic, fumaric, oxalic, methanesulfonic, ethanesulfonic, camphoric and citric acid.

Among the bases that may be used to form a pharmaceutically-acceptable addition salt with the compounds of the invention there may be mentioned by way of example, and in a non-limiting manner, sodium, potassium, calcium and aluminium hydroxides, alkali metal and alkaline earth metal carbonates, and organic bases, such as triethylamine, benzylamine, diethanolamine, tert-butylamine, dicyclohexylamine and arginine.

The present invention extends also to a process for the preparation of compounds of the general formula (I) which is characterised in that a compound of formula (II):

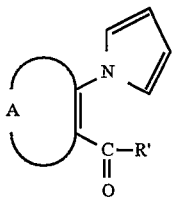
(II)

wherein A is as defined for formula (I) and R' represents a hydroxy, alkoxy or

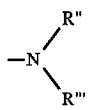

radical wherein R" and R'" are other than H and may be alkyls or may form together with the nitrogen atom carrying them a cyclic amine selected from pyrrolidine, piperidine and morpholine, is cyclised with phosphorus oxychloride in the presence or absence of a solvent, such as N,N-dimethylformamide (DMF), to obtain, after cyclisation, a tricyclic ketone of formula (III):

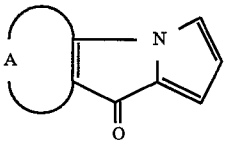
(III)

wherein A is as defined hereinbefore, which is then reacted with hydroxylamine to obtain an oxime of formula (IV):

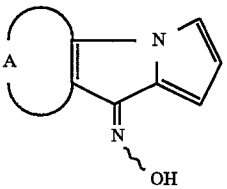
(IV)

wherein A is as defined hereinbefore, which may, if necessary and if desired, be separated into its E and Z isomers before being reacted with a compound of formula (V):

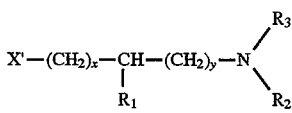
(V)

wherein $R_1$, $R_2$, $R_3$, x and y are as defined for formula (I) and X' represents a leaving group which may be a halogen or tosylate, to yield a compound of formula (I):

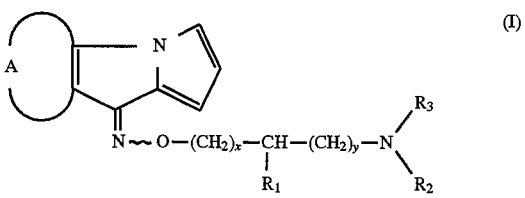
(I)

wherein A, $R_1$, $R_2$, $R_3$, x and y are as defined hereinbefore, which may, if necessary and if desired, be separated into its Z and E isomers and into its possible enantiomers or diastereoisomers, and/or be converted into a salt with a pharmaceutically-acceptable acid or base.

The present invention relates also to a process for the preparation of compounds of formula (I) which is characterised in that a compound of formula (II):

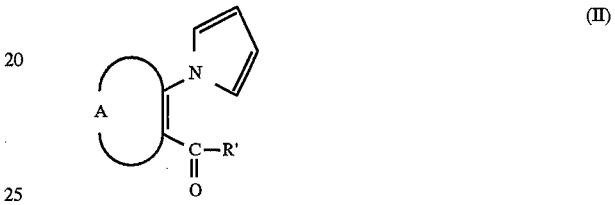
(II)

wherein A is as defined for formula (I) and R' represents a hydroxy, alkoxy or

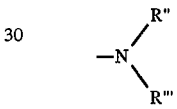

radical wherein R" et R'" are other than H and may represent alkyls or may form together with the nitrogen atom carrying them a cyclic amine selected from pyrrolidine, piperidine and morpholine, is cyclised with phosphorus oxychloride in the presence or absence of a solvent, such as DMF, to obtain, after cyclisation, a tricyclic ketone of formula (III):

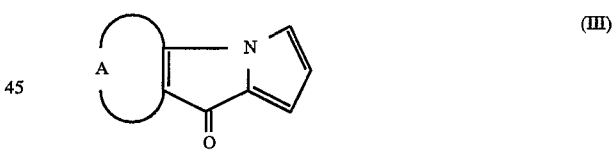
(III)

wherein A is as defined hereinbefore, which is then reacted with an amine of formula (VI):

$$H_2N-O-(CH_2)_x-\underset{\underset{R_1}{|}}{CH}-(CH_2)_y-X' \quad (VI)$$

wherein $R_1$, x and y are as defined for formula (I) and X' represents a leaving group, such as a halogen or tosylate, to obtain a compound of formula (VII):

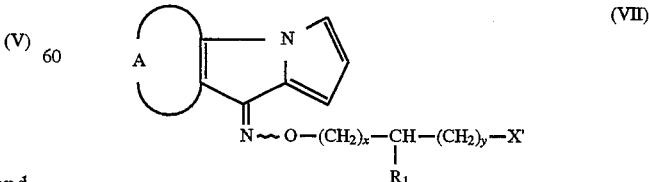
(VII)

wherein A, $R_1$, X', x and y are as defined hereinbefore, which may:

a) either be reacted with an amine of formula (VIII):

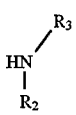
(VIII)

wherein $R_2$ and $R_3$ are as defined for formula (I), to yield a compound of formula (I):

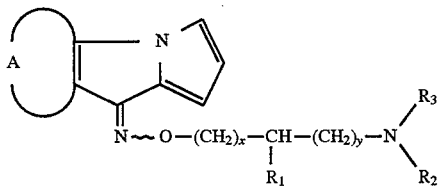
(I)

wherein A, $R_1$, $R_2$, $R_3$, x and y are as defined hereinbefore, which may, if necessary and if desired, be separated into its Z and E isomers and into its possible enantiomers or diastereoisomers and/or be converted into a salt with a pharmaceutically-acceptable acid or base, b) or be reacted with potassium phthalimide to obtain a phthalimide of formula (IX):

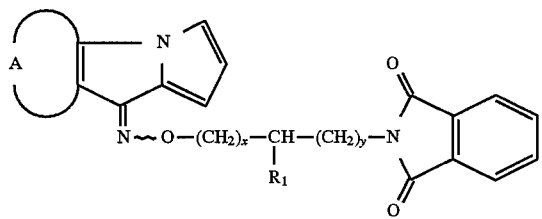
(IX)

wherein A, $R_1$, x and y are as defined hereinbefore, which is then hydrolysed in the presence of hydrazine to yield a compound of formula ($I_A$):

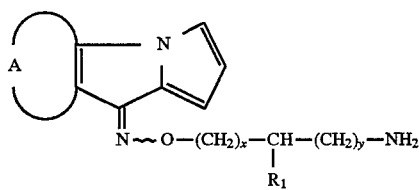
($I_A$)

wherein A, $R_1$, x and y are as defined hereinbefore, a particular case of compounds of formula (I) wherein $R_2=R_3=H$, which may, if necessary and if desired, be separated into its Z and E isomers and into its possible enantiomers or diastereoisomers, and/or be converted into a salt with a pharmaceutically-acceptable acid or base, which compound of formula ($I_A$) may, if desired, be alkylated with a compound of formula (X):

X'—$R_5$ (X)

wherein X' is as defined hereinbefore and $R_5$ has the same meaning as $R_2$, with the proviso that $R_5$ cannot represent either hydrogen or optionally substituted phenyl, to yield a compound of formula ($I_B$):

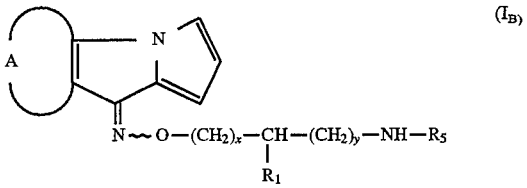
($I_B$)

wherein A, $R_1$, $R_5$, x and y are as defined hereinbefore, a particular case of compounds of formula (I), which may, if necessary and if desired, be separated into its Z and E isomers and into its possible enantiomers or diastereoisomers and/or be converted into a salt with a pharmaceutically-acceptable acid or base.

The present invention relates also to a process for the preparation of compounds of formula ($I_C$):

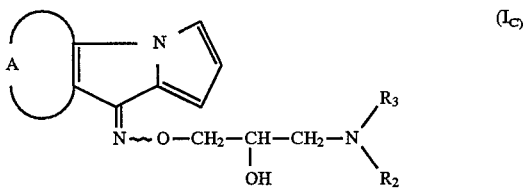
($I_C$)

a particular case of compounds of the general formula (I) wherein A, $R_2$ and $R_3$ are as defined for formula (I) with x=y=1 and $R_1$ representing a hydroxy group, characterised in that a compound of formula (II):

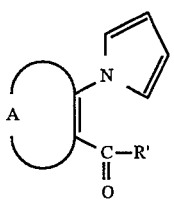
(II)

wherein A is as defined hereinbefore and R' represents a hydroxy, alkoxy or

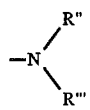

radical wherein R" and R''' are other than H and may be alkyls or may form together with the nitrogen atom carrying them a cyclic amine selected from pyrrolidine, piperidine and morpholine, is cyclised with phosphorus oxychloride in the presence or absence of a solvent, such as DMF, to yield, after cyclisation, a tricyclic ketone of the general formula (III):

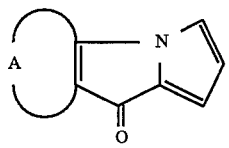
(III)

wherein A is as defined hereinbefore, which is then reacted with hydroxylamine to obtain an oxime of the general formula (IV):

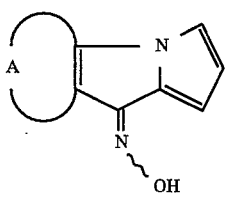

(IV)

wherein A is as defined hereinbefore, which may, if necessary and if desired, be separated into its E and Z isomers before being reacted, after metallisation with a metallic hydride, such as sodium hydride, with an epihalohydrin of the general formula (XI):

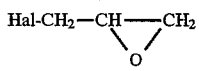

(XI)

wherein Hal represents a halogen atom, to yield, after reaction of the so-formed intermediate compound with an amine of the general formula (VIII):

(VIII)

wherin $R_2$ and $R_3$ are as defined hereinbefore, a compound of formula ($I_C$) as defined hereinbefore, which may, if necessary and if desired, be separated into its Z and E isomers and into its possible enantiomers or diastereoisomers, and/or be converted with an acid or a base into pharmaceutically-acceptable salts.

The compounds of the general formulae (I), ($I_A$), ($I_B$), ($I_C$) and also the synthesis intermediates used in the above-described processes may, if necessary, be purified according to one or more methods of purification selected from crystallisation, chromatography on a silica column, HPLC on a chiral or non-chiral phase, extraction, filtration and passage over charcoal and/or resin.

The starting materials used in the above-described processes are either commercial products or are readily obtainable by the person skilled in the art in accordance with processes described in the literature or exemplified in the Preparations described hereinafter.

The compounds of formula (I) possess very valuable pharmacological properties.

The Applicant has discovered that the compounds of the invention, very selectively have a very high affinity for $5HT_3$ and/or $5HT_{2C}$ serotoninergic receptors and also for serotonin reuptake sites.

In addition to that very high affinity clearly proved in vitro by receptor binding studies (determination of the affinity), the activity of the compounds of the present invention has also been established in vivo in animal behaviour models (Example B and C of the present Application).

The compounds of the invention may thus be used in the prevention and treatment of anxiety, depression, stress, psychoses, compulsive obsessional disorders of schizophrenia, disorders of the central nervous system, migraine, memory disorders, eating behaviour disorders, disorders of food intake, alcoholism and pain, and also in the prevention and treatment of vomiting and disorders of gastric emptying.

The invention extends also to pharmaceutical compositions comprising as active ingredient at least one of the compounds of formula (I) in pure form or in the form of a mixture of isomers or one of its pharmaceutically-acceptable addition salts with an acid or a base, in combination with one or more pharmaceutically-acceptable excipients or carriers.

Among the compositions according to the invention there may be mentioned by way of example, and in a non-limiting manner, those which are suitable for oral, parenteral, ocular, per- or trans-cutaneous, nasal, rectal, perlingual or respiratory administration, and especially injectable preparations, aerosols, eye or nose drops, tablets, sublingual tablets, soft gelatin capsules, hard gelatin capsules, lozenges, glossettes, suppositories, creams, ointments and gels.

The preparations so obtained are generally presented in dosage form and may contain, depending on the disorders treated and the weight, age and sex of the patient, from 0.01 to 100 mg of active ingredient taken from one to three times per day, preferably from 0.01 to 5 mg of active ingredient, especially from 0.1 to 5 mg, for example 1 mg.

The following Examples illustrate the invention but do not limit it in anyway.

PREPARATION 1

Methyl 3-(pyrrol-1-yl)thiophene-2-carboxylate

At room temperature, add 20 g (0.127 mol) of methyl 3-aminothiophene-2-carboxylate in small portions to a solution of 16.80 g (0.127 mol) of 2,5-dimethoxytetrahydrofuran in 100 ml of acetic acid. After 30 minutes' stirring at room temperature, then 90 minutes at 90° C., the acetic acid is removed under reduced pressure and the residue is taken up in 100 ml of 2N sodium hydroxide solution and extracted with diethyl ether. After washing with water and rendering colourless with animal charcoal, the ethereal phase is concentrated to dryness to yield the title compound.

Yield: 68%

Melting point: 60° C.

Infrared: $\nu$ cm$^{-1}$(KBr): 1700 (CO)

PREPARATION 2

3-(Pyrrol-1-yl)thiophene-2-carboxylic acid

A solution of 20 g (0.096 mol) of methyl 3-(pyrrol-1-yl) thiophene-2-carboxylate in a mixture of 150 ml of methanol and 100 ml of a 6N aqueous sodium hydroxide solution is heated at reflux, with stirring, for 3 hours. The methanol is removed under reduced pressure and the reaction mixture is diluted with 100 ml of acidified water and extracted with 500 ml of ether. The ethereal phase is decanted off, dried and then concentrated in vacuo, and the title compound is recrystallised from diethyl ether.

Yield: 74%

Melting point: 170° C.

Infrared: $\nu$ cm$^{-1}$(KBr): 1675 (CO), 2980 and 2520 (OH)

PREPARATION 3

Methyl 4-methyl-3-(pyrrol-1-yl)thiophene-2-carboxylate 43.8 g (0.292 mol) of 4-chloropyridine hydrochloride and 38.59 g (0.292 mol) of 2,5-dimethoxytetrahydrofuran are stirred for 10 minutes at room temperature in 600 ml of dioxane. 50 g (0.292 mol) of methyl 4-methyl-3-aminothiophene-2-carboxylate are added and the suspension is heated at reflux for 3 hours. The dioxane is removed under reduced pressure, and the residue is taken up in 1 liter of water and then extracted with 1 liter of diethyl ether. The ethereal phase is washed with water, decanted off, dried over magnesium sulfate, rendered colourless with animal charcoal and concentrated under reduced pressure to yield the title compound.

Yield: 91%

Melting point: 76° C.

Infrared: ν cm⁻¹(KBr): 1715 (CO)

PREPARATIONS 4 TO 8

By proceeding in the same manner as for Preparations 1 and 3, but using suitably substituted methyl thiophenecarboxylates, the compounds corresponding to Preparations 4 to 8 are obtained.

PREPARATION 10

4,5-Dimethyl-2-(pyrrol-1-yl)thiophene-3-carboxylic acid

The title compound is obtained by proceeding as for Preparation 2.

Yield: 84%

Melting point: 156° C.

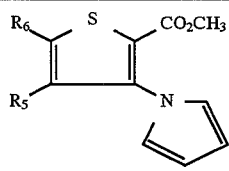

| Preparation | R₆ | R₅ | ν cm⁻¹ (KBr) | Melting point | Yield | Recrystallisation solvent |
|---|---|---|---|---|---|---|
| 4 | CH₃—C₆H₄— | H | 1710 (CO) | 104° C. | 76% | diethyl ether |
| 5 | CH₃O—C₆H₄— | H | 1700 (CO) | 91° C. | 82% | diehyl ether |
| 6 | H | Cl—C₆H₄— | 1720 (CO) | 178° C. | 85% | ethanol |
| 7 | H | F—C₆H₄— | 1720 (CO) | 140° C. | 70% | ethanol |
| 8 | H | Br—C₆H₄— | 1710 (CO) | 173° C. | 92% | acetonitrile |

PREPARATION 9

Ethyl 4,5-dimethyl-2-(pyrrol-1-yl)thiophene-3-carboxylate

By proceeding as for Preparation 1, the title compound is obtained in the form of an oil.

Yield: 91%

Infrared: ν cm⁻¹(KBr): 1720 (C=O)

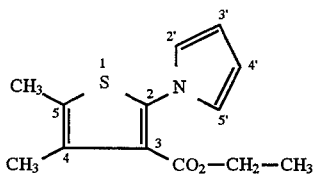

¹H NMR: δ (ppm) (DMSO d₆): 1.47 triplet (3H, CH₂CH₃); 2.57 singlet (3H, CH₃₍₄₎); 2.67 singlet (3H, CH₃₍₅₎); 4.47 quadruplet (2H, CH₂); 6.50 doublet of doublet (2H, H₃', H₄'); 7.20 doublet of doublet (2H, H₂', H₅').

Infrared: ν cm⁻¹(KBr): 2530 (OH), 1670 (C=O)

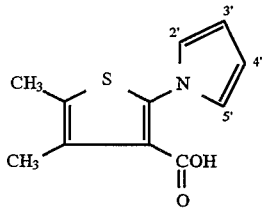

¹H NMR: δ (ppm) (DMSO d₆): 2.28 singlet (3H, CH₃₍₄₎); 2.50 singlet (3H, CH₃₍₅₎); 6.13 doublet of doublet (2H, H₃', H₅'); 6.84 doublet of doublet (2H, H₂', H₅').

PREPARATION 11

N-[3-(Pyrrol-1-yl)thiophen-2-ylcarbonyl]pyrrolidine

Heat a suspension of 10 g (0.048 mol) of methyl 3-(pyrrol-1-yl)thiophene-2-carboxylate in 40 ml of pyrroli dine at reflux for 7 hours. The solution is poured into 800 ml of cold water, with stirring, and the precipitate formed is suction-filtered, washed with cold water, and then recrystallised from diethyl ether.

Yield: 88%

Melting point: 110° C. (diethyl ether)

Infrared: ν cm$^{-1}$(KBr): 1600 (C=O)

PREPARATION 12

N-[3-(Pyrrol-1-yl)thiophen-2-ylcarbonyl]morpholine

By proceeding in the same manner as for Preparation 11, but using morpholine instead of pyrrolidine, the title compound is obtained in the form of white crystals.

Yield: 84%

Melting point: 100° C. (diethyl ether)

Infrared: ν cm$^{-1}$(KBr): 1615 (C=O)

By proceeding in the same manner as for Preparation 11, but using methyl 4-methyl-3-(pyrrol-1-yl)thiophene-2-carboxylate, the title compound is obtained in the form of white crystals.

Yield: 83%

Melting point: 178° C.

Infrared: ν cm$^{-1}$(KBr): 1610 (C=O)

PREPARATIONS 15 TO 19

By proceeding in the same manner as for Preparation 11, but replacing the methyl 3-(pyrrol-1-yl)thiophene-2-carboxylate with the esters corresponding to Preparations 4 to 8, the compounds corresponding to Preparations 15 to 19 are obtained.

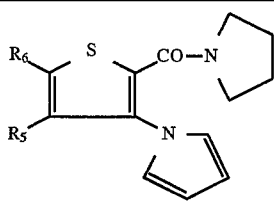

| Preparation | R$_6$ | R$_5$ | ν cm$^{-1}$ (KBr) | Melting point | Yield | Recrystallisation solvent |
|---|---|---|---|---|---|---|
| 15 | CH$_3$—⟨phenyl⟩— | H | 1625 (CO) | 139° C. | 80% | diethyl ether |
| 16 | CH$_3$O—⟨phenyl⟩— | H | 1620 (CO) | 154° C. | 60% | acetonitrile |
| 17 | H | Cl—⟨phenyl⟩— | 1620 (CO) | 200° C. | 60% | acetonitrile |
| 18 | H | F—⟨phenyl⟩— | 1620 (CO) | 144° C. | 70% | ethanol |
| 19 | H | Br—⟨phenyl⟩— | 1610 (CO) | 209° C. | 58% | acetonitrile |

PREPARATION 13

N-[3-(Pyrrol-1-yl)thiophen-2-ylcarbonyl]piperidine

By proceeding in the same manner as for Preparation 11, but using piperidine instead of pyrrolidine, the title compound is obtained in the form of yellow crystals.

Yield: 80%

Melting point: 126° C. (diethyl ether)

Infrared: ν cm$^{-1}$(KBr): 1625 (C=O)

PREPARATION 14

N-[3-(Pyrrol-1-yl)-4-methylthiophen-2-ylcarbonyl] pyrrolidine

PREPARATION 20

N-[4,5-Dimethyl-2-(pyrrol-1-yl)thiophen-3-ylcarbonyl]pyrrolidine

Step A: 4,5-Dimethyl-2-(pyrrol-1-yl)thiophene-3-carbonyl chloride 4.45 g (20.1 mmol) of 4,5-dimethyl-2-(pyrrol-1-yl) thiophene-3-carboxylic acid (Preparation 10) are dissolved in 150 ml of benzene at 10° C., then 5.85 g (28.1 mmol) of phosphorus pentachloride are gently added. After 1 hours' stirring at 10° C., then 2 hours at room temperature, the reaction mixture is filtered and the benzene is removed under reduced pressure. The residue is taken up in 500 ml of n-hexane and then filtered, and the n-hexane is removed under reduced pressure. The acid chloride obtained is used directly in Step B.

Step B: N-[4,5-Dimethyl-2-(pyrrol-1-yl)thiophen-3-ylcarbonyl]pyrrolidine

The acid chloride obtained in Step A is dissolved in 25 ml of benzene at 0° C. and then 2.92 ml of triethylamine and 13.5 ml of pyrrolidine are added dropwise in succession. The reaction mixture is stirred for one hour and then diluted with 50 ml of water, acidified with, 10N hydrochloric acid and extracted with 300 ml of diethyl ether. The ethereal phase is washed with water, dried over magnesium sulfate, rendered colourless with animal charcoal and concentrated under reduced presure to yield the title compound.

Yield: 74%

Melting point: 100° C.

Infrared: ν cm$^{-1}$(KBr): 1615 (C=O)

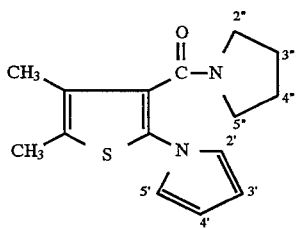

$^1$H NMR: δ (ppm) (DMSO d$_6$): 1.70 multiplet (4H, H$_{3''}$, H$_{4''}$); 2.00 singlet (3H, CH$_{3(4)}$); 2.33 singlet (3H, CH$_{3(5)}$); 3.33 multiplet (4H, H$_{2''}$, H$_{3''}$); 6.20 triplet (2H, H$_{3'}$, H$_{4'}$); 6.87 triplet (2H, H$_{2'}$, H$_{5'}$).

PREPARATION 21

N-[2-(Pyrrol-1-yl)thiophen-3-ylcarbonyl]pyrrolidine

Add 50 ml of pyrrolidine dropwise, at room temperature, to a solution of 2-(pyrrol-1-yl)thiophen-3-ylcarbonyl azide (Heterocycles, (1983), 20, 477) in 500 ml of dichloromethane. The reaction mixture is stirred for 12 hours at room temperature and then washed three times with 150 ml of 1N hydrochloric acid each time and then with 150 ml of water. The organic phase is then dried over calcium chloride and subsequently concentrated to dryness to yield the title compound in the form of an oil.

Yield: 73%

Infrared: ν cm$^{-1}$(KBr): 1610 (C=O)

$^1$H NMR: δ (ppm) (DMSO d$_6$): 1.66 multiplet (4H); 2.80 multiplet (2H); 3.30 multiplet (2H); 6.20 multiplet (2H, H$_{3'}$, H$_{4'}$); 6.90 multiplet (2H, H$_{2'}$, H$_{5'}$); 7.03 doublet (1H, H$_4$); 7.31 doublet (1H, H$_5$)

PREPARATION 22

5-Chloro-2-(pyrrol-1-yl)benzoic acid 18.6 ml (0.143 mol) of 2,5-dimethoxytetrahydrofuran are stirred for 10 minutes with 21.5 g (0.143 mol) of 4-chloropyridine hydrochloride in 600 ml of 1,4-dioxane. 24.6 g (0.143 mol) of 2-amino-4-chlorobenzoic acid are added, and the mixture is heated at reflux for 4 hours. After removal of the dioxane under reduced pressure, the residue is taken up with 1 liter of water and extracted with 800 ml of diethyl ether. The ethereal phase is washed with water and then extracted with 500 ml of a saturated aqueous sodium hydrogen carbonate solution. The aqueous phase is acidified with 10N hydrochloric acid and then extracted with 800 ml of diethyl ether. The ethereal phase is washed with water, decanted off, dried over magnesium sulfate, rendered colourless with animal charcoal and concentrated under reduced pressure to yield the title compound in the form of a grey powder.

Yield: 95%

Melting point: 178° C.

Infrared: ν cm$^{-1}$(KBr): 3000 (COOH), 1680 (C=O)

PREPARATION 23

N-[5-Chloro-2-(pyrrol-1-yl)benzoyl]pyrrolidine

Step A: 5-Chloro-2-(pyrrol-1-yl)benzoyl chloride 10 g (45.1 mmol) of 5-chloro-2-pyrrol-1-ylbenzoic acid are dissolved in 300 ml of benzene at 10° C. and then 13.15 g (63.1 mmol; 1.4 eq.) of phosphorus pentachloride are gently added. After 1 hours' stirring at 10° C., then 2 hours at room temperature, the reaction mixture is filtered and the benzene is removed under reduced pressure. The residue is taken up in 500 ml of n-hexane and then filtered and the n-hexane is removed under reduced pressure. The acid chloride is obtained in the form of a red oil which is used directly in Step B.

Infrared: ν cm$^{-1}$: 3100 (CH), 1755 (C=O)

Step B: N-[5-Chloro-2-(pyrrol-1-yl)benzoyl]pyrrolidine

The acid chloride obtained in Step A is dissolved in 50 ml of benzene at 0° C., and 6.5 ml of triethylamine followed by 30 ml of pyrrolidine are added dropwise. The reaction mixture is stirred for 1 hour and then diluted with 100 ml of water, acidifed to pH=4 with 10N hydrochloric acid, and extracted with 300 ml of diethyl ether. The ethereal phase is washed with water, dried over magnesium sulfate, rendered colourless with animal charcoal and concentrated under reduced pressure to yield the title compound in the form of an oil.

Yield: 79%

Infrared: ν cm$^{-1}$(KBr): 3100 (=C—H), 1620 (C=O)

PREPARATION 24

5-Methyl-2-(pyrrol-1-yl)benzoic acid

The title compound is obtained by proceeding in the same manner as for Preparation 22, but using the appropriate reactants.

Yield: 77%

Melting point: 124° C.

Infrared: ν cm$^{-1}$(KBr): 3430 (OH), 1675 (C=O)

PREPARATION 25

N-[5-Methyl-2-(pyrrol-1-yl)benzoyl]pyrrolidine

The title compound is obtained by proceeding in the same manner as for Preparation 23, Steps A and B, but using 5-methyl-2-(pyrrol-1-yl)benzoic acid as starting material.

Yield: 42% in two stages

Melting point: 69° C.

Infrared: ν cm$^{-1}$: 2930–2880 (=C—H), 1630(C=O)

PREPARATION 26

2-(Pyrrol-1-yl)benzoic acid

Method A

The title compound is obtained by proceeding in the same manner as for Preparations 22 and 24, but using the appropriate reactants.

Yield: 91.8%

Melting point: 98° C.

Infrared: ν cm$^{-1}$(KBr): 3460 (OH), 1680 (C=O)

Method B

Step A: Methyl 2-(pyrrol-1-yl)benzoate 17.14 mol of 2,5-dimethoxytetrahydrofuran and 19.84 g of 4-chloropyridine hydrochloride in 600 ml of 1,4-dioxane are stirred for 10 minutes at 25° C., and then 17.12 mol of methyl anthranilate are added and the suspension is heated at reflux for 3 hours. After removal of the dioxane under reduced pressure, the residue is taken up in 1 liter of water and extracted with diethyl ether. The ethereal phase is washed with water, decanted off, dried over magnesium sulfate, rendered colourless with animal charcoal, and then concentrated under reduced pressure to yield the title product in the form of an oil.

Yield: 92.7%

Infrared: ν cm$^{-1}$(KBr): 2940 (=C—H), 1710(CO$_2$CH$_3$)

Step B: 2-(Pyrrol-1-yl)benzoic acid 24 g of the ester obtained in the preceding Step are dissolved in a mixture of 75 ml of methanol and 75 ml of an aqueous 30% sodium hydroxide solution. After 5 hours' heating at reflux, the methanol is removed under reduced pressure, the residue is taken up in wetter and acidified with 10N hydrochloric acid, and the precipitate is isolated by filtration. The precipitate is taken up in diethyl ether and then the ethereal phase is washed with water, dried over magnesium sulfate, rendered colourless with animal charcoal and then concentrated under reduced pressure to give the title compound in a yield of 65%.

Total yield: 60%

PREPARATION 27

4-Chloro-2-(pyrrol-1-yl)benzoic acid

The title compound is obtained by proceeding in the same manner as for Preparations 22 and 24, but using the appropriate reactants.

Yield: 88.2%

Melting point: 139° C.

Infrared: ν cm$^{-1}$(KBr) 1670 (C=O)

PREPARATION 28

8H-Thieno[2,3-d]pyrrolo[1,2-a]pyrrol-8-one

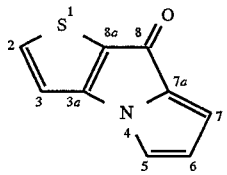

A suspension of 0.04 mol of N-[3-(pyrrol-1-yl)thiophen-2-ylcarbonyl]pyrrolidine (Preparation 11) in 90 ml of phosphorus oxychloride is heated at reflux for 1 hour. After cooling, the imminium salt formed is isolated by filtration, washed with petroleum ether and then diethyl ether, dried, and then dissolved in water. The aqueous phase is rendered alkaline by the dropwise addition of 2N sodium hydroxide solution and then, after 1 hours' stirring, the precipitate formed is isolated by filtration, washed with water, dried and then recrystallised from diethyl ether.

Yield: 77%

Melting point: 112° C.

Infrared: ν cm$^{-1}$(KBr): 1670 (C=O)

This compound can also be obtained by using N-[3-(pyrrol-1-yl)thiophen-2-ylcarbonyl]morpholine (Preparation 12) and N-[3-(pyrrol-1-yl)thiophen-2-ylcarbonyl]piperidine (Preparation 13) as starting materials.

PREPARATIONS 29 TO 34

The compounds corresponding to Preparations 29 to 34 are obtained by proceeding in the same manner as for Preparation 28, but replacing the N-[3-(pyrrol-1-yl)thiophen-2-ylcarbonyl]pyrrolidine with the appropriate amide.

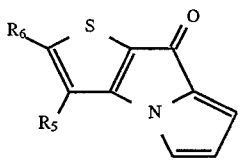

| Preparation | R₆ | R₅ | ν cm⁻¹ (KBr) | Melting point | Yield | Recrystallisation solvent |
|---|---|---|---|---|---|---|
| 29 | H | CH₃ | 1660 (CO) | 134° C. | 72% | diethyl ether |
| 30 | CH₃–C₆H₄– | H | 1650 (CO) | 196° C. | 60% | acetonitrile |
| 31 | CH₃–O–C₆H₄– | H | 1660 (CO) | 132° C. | 70% | diethyl ether |
| 32 | H | Cl–C₆H₄– | 1675 (CO) | 186° C. | 78% | acetonitrile |
| 33 | H | F–C₆H₄– | 1670 (CO) | 148° C. | 60% | ethanol |
| 34 | H | Br–C₆H₄– | 1670 (CO) | 164° C. | 62% | ethanol |

PREPARATION 35

8-Hydroxyiminothieno[2,3-d]pyrrolo[1,2-a]pyrrole

Heat at reflux for 90 minutes a solution of 0.011 mol of 8H-thieno[2,3-d]pyrrolo[1,2-a]pyrrol-8-one (Preparation 28) and 0.0132 mol of hydroxylamine hydrochloride in 50 ml of pyridine. After cooling and after removal of the pyridine under reduced pressure, the residue is taken up in 150 ml of water and extracted with diethyl ether. The ethereal solution is dried over magnesium sulfate and then concentrated under reduced pressure to yield the title compound in the form of a mixture comprising 70% of the Z form, 30% of the E form.

Yield: 82.8%

Melting point: 172° C.

Infrared: ν cm⁻¹(KBr): 3360 (OH)

PREPARATION 36

3-Methyl-8-hydroxyiminothieno[2,3-d]pyrrolo[1,2-a]pyrrole

By proceeding as for Preparation 35, the title compound is obtained in the form of a mixture comprising 70% of the Z form, 30% of the E form.

Yield: 92%

Melting point: 198° C. (70% Z, 30% E mixture)

Infrared: ν cm⁻¹(KBr): 1635 (C=N)

The 3-methyl-8-hydroxyiminothieno[2,3-d]pyrrolo[1,2-a]pyrrole may be obtained in the form of the pure Z isomer by recrystallisation of the mixture of Z and E isomers from acetonitrile.

Yield: 33%

Melting point: 204° C. (pure Z isomer)

¹H NMR: (DMSOd₆): δ(ppm): 2.03 singlet (3H,CH₃); 5.86 doublet of doublet (1H,H₆); 6.16 doublet (1H, H₇); 6.96 doublet (1H, H₅); 7.16 singlet (1H, H₂); 11.49 singlet (1H, =N—OH)

PREPARATION 37 TO 41

The compounds of Preparations 37 to 41 are obtained by proceeding as for Preparation 35, but using the compounds of Preparations 30 to 34 as starting materials.

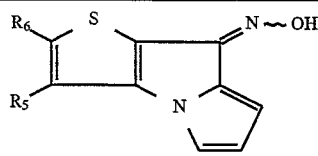

| Preparation | R₆ | R₅ | Melting point | Yield | Recrystallisation solvent | Isomerism |
|---|---|---|---|---|---|---|
| 37 | CH₃—C₆H₄— | H | 210° C. | 82% | acetonitrile | 100% Z |
| 38 | CH₃—O—C₆H₄— | H | 188° C. | 76% | acetonitrile | 80% Z<br>20% E |
| 39 | H | Cl—C₆H₄— | 210° C. | 80% | acetonitrile | 70% Z<br>30% E |
| 40 | H | F—C₆H₄— | 228° C. | 72% | acetonitrile | 100% Z |
| 41 | H | Br—C₆H₄— | 226° C. | 70% | acetonitrile | 100% Z |

PREPARATION 42

7-Chloropyrrolo[1,2-a]indol-9-one

A solution of 8.5 g (30.9 mmol) of N-[5-chloro-2-(pyrrol-1-yl)benzoyl]pyrrolidine (Preparation 23) in 70 ml of phosphorus oxychloride is heated at 100° C. for 35 minutes. After cooling, the precipitate formed is isolated by filtration, washed with petroleum ether to remove excess phosphorus oxychloride, and then redissolved in 30 ml of water. The aqueous solution is rendered alkaline by the dropwise addition of 10% sodium hydroxide solution and the precipitate formed is filtered and extracted with 100 ml of ethyl acetate. The organic phase is washed with water, dried over magnesium sulfate, rendered colourless with animal charcoal and concentrated under reduced pressure to yield 1.76 g of the title product.

Yield: 27%

Melting point: 92° C.

Infrared: ν cm⁻¹(KBr): 3090 (CH), 1675 (C=O)

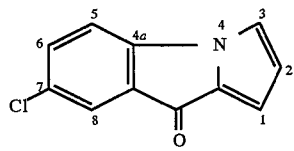

¹H NMR: δ(ppm): (DMSO d₆): 6.33 doublet of doublet (1H, H₂); 6.80 doublet of doublet (1H, H₁); 7.53-7.47-7.40 multiplet (4H, H₃, H₅, H₆, H₈)

PREPARATION 43

7-Methylpyrrolo[1,2-a]indol-9-one.

At 0° C., add 1.36 ml (14.9 mmol) of phosphorus oxychloride to 1.14 ml (14.9 mmol) of dimethylformamide, then add a solution of 3 g (14.9 mmol) of 5-methyl-2-pyrrol-1-ylbenzoic acid (Preparation 25) in 30 ml of dimethylformamide. After one night's stirring at room temperature, hydrolyse the reaction mixture by pouring into 50 ml of water, extract with 200 ml of diethyl ether, and wash the ethereal phase in succession with water, a saturated aqueous hydrogen carbonate solution and then water. After drying over magnesium sulfate and rendering colourless with animal charcoal, the ethereal phase is concentrated to dryness to yield the title compound.

Yield: 35%

Melting point: 85° C.

Infrared: ν cm⁻¹(KBr): 1670 (C=O)

PREPARATIONS 44 AND 45

The following are obtained by proceeding in the same manner as for Preparation 43:

PREPARATION 44

Pyrrolo[1,2-a]indol-9-one

Yield: 50%

Melting point: 126° C.

Infrared: ν cm⁻¹(KBr): 1670 (C=O)

PREPARATION 45

6-Chloropyrrolo[1,2-a]indol-9-one

Yield: 35%

Melting point: 181° C.

Infrared: ν cm⁻¹(KBr): 1670 (C=O)

PREPARATION 46

7-Chloro-9-hydroxyiminopyrrolo[1,2-a]indole

Add 3.9 g (56.1 mmol) of hydroxylamine hydrochloride to a solution of 4.6 g (22.6 mmol) of 7-chloropyrrolo[1,2-a]indol-9-one in 80 ml of pyridine, then heat the reaction mixture at reflux for 3 hours. After cooling, the pyridine is removed under reduced pressure and the residue is taken up in water and extracted with 300 ml of diethyl ether. The ethereal phase is washed with 100 ml of 0.5N hydrochloric acid and then with water, dried over magnesium sulfate, rendered colourless with animal charcoal and then concentrated under reduced pressure to yield 4.18 g of the title product.

Yield: 84.6%

Melting point: 211° C.

Infrared: ν cm⁻¹(KBr): 3180, 3060, 2880, 1490

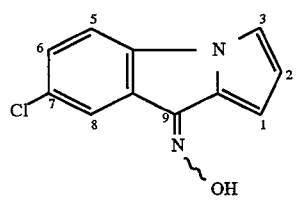

$^1$H NMR: δ(ppm) (DMSO d$_6$): 6.40 doublet of doublet (1H, H$_2$); 6.70 doublet of doublet (1H, H$_1$); 7.65-7.55 multiplet (4H, H$_3$, C$_6$H$_3$); 12.27 singlet (1H, OH)

PREPARATIONS 47 TO 49

The compounds of Preparations 47, 48 and 49 are obtained by proceeding as for Preparation 46 but using the compounds of Preparations 43, 44 et 45 as starting materials.

| Preparation | R$_5$ | R$_6$ | Melting point | Yield | $^1$H NMR δ (ppm) (DMSO d6) |
|---|---|---|---|---|---|
| 47 | H | CH$_3$ | 187° C. | 77% | 2.35(s, 3H); 6.33(dd, 1H); 6.65(dd, 1H); 7.43-7.25(m, 4H); 11.43(s, OH) |
| 48 | H | H | 186° C. | 80% | 6.35(dd, 1H); 6.65(dd, 1H); 7.50-7.23-7.13(m, 5H); 11.97(m, 1H) |
| 49 | Cl | H | 195° C. | 84% | 6.38(dd, 1H); 6.67(dd, 1H); 7.17(dd, 1H); 7.57(m, 2H); 7.77(d, 1H); 12.10(s, 1H) |

PREPARATION 50

1,2-Dimethyl-8H-thieno[3,2-d]pyrrolo[1,2-a]pyrrol-8-one

A solution of 7.6 g of N-[4,5-dimethyl-2-(pyrrol-1-yl)thiophen-3-ylcarbonyl]pyrrolidine (Preparation 20) in 50 cm³ of phosphorus oxychloride is heated at 100 ° C. for 35 minutes. After cooling, the precipitate formed is isolated by filtration, washed with petroleum ether to remove excess phosphorus oxychloride and then redissolved in 25 ml of water. The aqueous solution is rendered alkaline with 10% sodium hydroxide solution and the precipitate formed is filtered and extracted with 100 ml of ethyl acetate. The organic phase is washed with water, dried over magnesium sulfate, rendered colourless with animal charcoal and concentrated under reduced pressure to yield 2.8 g of the title product.

Yield: 49.7%

Melting point: 95° C. (decomposition)

Infrared: ν cm⁻¹(KBr): 1670 (C=O)

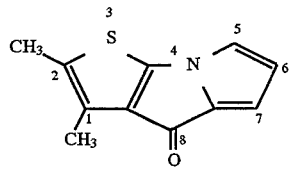

$^1$H NMR: δ(ppm) (DMSO d$_6$): 2.03 singlet (3H, CH$_{3(1)}$); 2.20 singlet (3H, CH$_{3(2)}$); 6.05 doublet of doublet (1H, H$_6$); 6.93 doublet of doublet (1 H, H$_7$); 7.20 doublet of doublet (1H, H$_5$)

PREPARATION 51

8H-Thieno[3,2-d]pyrrolo[1,2-a]pyrrol-8-one

The title compound is obtained by proceeding as for Preparation 50, but using N-[2-(pyrrol-1-yl)thiophen-3-ylcarbonyl]pyrrolidine (Preparation 21).

PREPARATION 52

1,2-Dimethyl-8-hydroxyiminothieno[3,2-]pyrrolo[1,2-a]pyrrole

The title compound is obtained as for Preparation 46, but using 1,2-dimethyl-8H-thieno[3,2-d]pyrrolo[1,2-a]pyrrol-8-one (Preparation 50) as starting material.

Yield: 83%

Melting point: decomposition from 180° C.

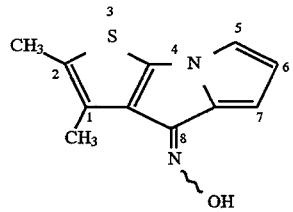

$^1$H NMR: δ(ppm) (DMSO d$_6$): 2.17 singlet (3H, CH$_{3(1)}$); 2.30 singlet (3H, CH$_{3(2)}$); 6.13 doublet of doublet (1H, H$_6$); 6.53 doublet of doublet (1H, H$_7$); 7.15 doublet of doublet (1H, H$_5$)

PREPARATION 53

8-Hydroxyiminothieno[3,2-d]pyrrolo[1,2-a]pyrrole

The title compound is obtained by proceeding as for Preparation 52, but using 8H-thieno[2,3-b]pyrrolo[2,1-e]pyrrol-8-one (Preparation 51) as starting material.

Yield: 90%

Melting point: 250° C. E isomer; 190° C. Z isomer

Infrared: ν cm$^{-1}$(KBr): 1635 (C=N)

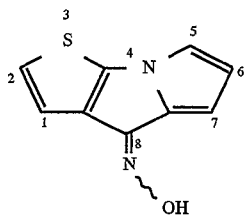

$^1$H NMR: δ(ppm) (DMSO d$_6$): E isomer: 6.15 (1H, H$_6$); 6.60 (1H, H$_7$); 7.03 (2H, H$_1$, H$_2$); 7.27 (1H, H$_5$); Z isomer: 6.12 (1H, H$_6$); 6.37 (1H, H$_7$); 7.05 (1H, H$_2$); 7.21 (1H, H$_1$) 7.26 (1H, H$_5$)

EXAMPLE 1

8-[(3-Isopropylamino-2-hydroxy-n-prop-1-yloxy) imino]thieno[2,3-d]pyrrolo-[1,2-a]pyrrole

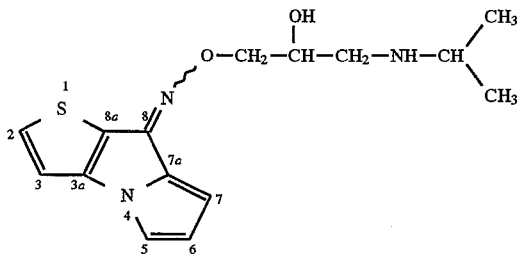

Step A: (Z)-8-[(2,3-Epoxyprop-1-yl)oxyimino] thieno[2,3-d]pyrrolo[2,1-a]pyrrole

Add 0.8 g of sodium hydride to a solution of 4 g (0.021 mole) of 8-hydroxyiminothieno[2,3-d]pyrrolo[1,2-a]pyrrole in 50 ml of toluene and 10 ml of dimethylformamide. Wait for 15 minutes and then add 2.85 g (0.021 mole) of epibromohydrin. After 7 hours' stirring at room temperature, the reaction mixture is poured into 200 ml of water, decanted off, dried and then concentrated to dryness under reduced pressure. The solid obtained is recrystallised from cyclohexane to yield the Z isomer.

Yield: 35%

Melting point: 100° C.

Infrared: ν cm$^{-1}$(KBr): 1600 (C=N)

Step B: 8-[3-1Isopropylamino-2-hydroxyprop-1-yloxy)imino]thieno[2,3-d]pyrrolo[1,2-a]pyrrole 2 g of 8-[(2,3-epoxyprop-1-yl)oxyimino]thieno[2,3-d] pyrrolo[1,2-a]pyrrole (Z) are added to 5 ml of an aqueous solution of isopropylamine, then stirred for 10 hours at room temperature. After hydrolysis and extraction with diethyl ether, the residual oil obtained is dissolved in 30 ml of isopropanol at 40° C. After the addition of one equivalent of oxalic acid, the precipitate formed is suction-filtered, washed with ether and recrystallised from an isopropanol/ propanol (60:40) mixture.

Yield: 65% (oxalate)

Melting point: oxalate 196° C. (50/50 Z/E mixture)

Infrared: ν cm$^{-1}$(KBr): (oxalate) 3120-2600 (NH$_{2+}$), 1700 (C=O)

EXAMPLE 2

8-[(3-Cycloheptylamino-2-hydroxyprop-1-yloxy) imino]thieno[2,3-d]pyrrolo-[1,2-a]pyrrole The title compound is obtained by proceeding as for Example 1, but replacing the isopropylamine in Step B with cycloheptylamine.

Yield: 51%

Melting point: base: 118° C.: (50/50 Z/E mixture); oxalate: 186° C.: (50/50 Z/E mixture)

EXAMPLE 3

(Z)-8-{[2-(N,N-Dimethylamino)ethoxy]imino}-3-methylthieno[2,3-d]pyrrolo-[1,2-a]pyrrole 1.32 g of water and then 3.91 g of 1-chloro-2-(N,N-dimethylamino)ethane hydrochloride and 5 g of (Z)-8-hydroxyimino-3-methylthieno[2,3-d]pyrrolo[1,2-a]pyrrole (Preparation 36) are added to 6.99 g of sodium carbonate in 200 ml of anhydrous acetone. The reaction mixture is heated at reflux for 40 hours, then the acetone is removed and the residue is taken up in 100 ml of water and then extracted with 200 ml of diethyl ether. The ethereal phase is washed with water, decanted off and then dried over magnesium sulfate, and subsequently concentrated to dryness to yield the title product in the form of an oil.

Yield: 77%

Preparation of the oxalate salt 4.9 g of the oil obtained above are dissolved in 50 ml of isopropanol at 40° C. and then 1.68 g of oxalic acid are added and the whole is heated at reflux for 30 minutes. After cooling, the precipitate is isolated by filtration, washed with diethyl ether and then dried to yield the title product in the form of the oxalate.

Yield: 68%

Melting point: 200° C.

Infrared: ν cm$^{-1}$(KBr): 3006, 2700, 2540, 2500, 1725, 1610.

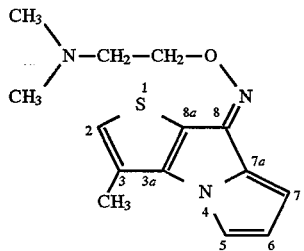

$^1$H NMR: δ(ppm) (DMSO d$_6$): 2.36 singlet (3H, CH$_3$); 2.80 singlet (6H, 2×CH$_3$); 3.43 multiplet (2H, CH$_2$); 4.60 multiplet (2H, CH$_2$); 6.20 split doublet (1H, H$_6$); 6.53 split doublet (1H, H$_7$); 7.30 split doublet (1H, H$_5$); 7.56 singlet (1H, H$_2$); 10.40 singlet (1H, NHO)

Using 8-hydroxyiminothieno[2,3-d]pyrrolo[1,2-a]pyrrole in the form of a 70% Z/30% E mixture as starting material, the title compound is obtained in the form of a mixture of isomers in proportions equivalent to the starting proportions.

EXAMPLES 4 TO 38

By proceeding in the same manner as for Example 3, but using the appropriate aminohaloalkyl and 8-hydroxyiminothieno[2,3-d]pyrrolo[1,2-a]pyrrole, the compounds of the following Examples are obtained:

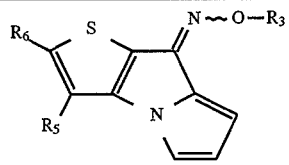

| Ex. | R₆ | R₅ | R₃ | Salt | Yield | Isomer | Melting point | Infrared ν (cm⁻¹) |
|---|---|---|---|---|---|---|---|---|
| 4 | H | H | —(CH₂)₂—N(CH₃)₂ | oxalate | 60% | Z/E 80/20 | 168° C. (acetonitrile) | 1630 (C=N); 2480, 2680 (NH+) |
| 5 | H | H | —CH₂—CH(CH₃)—N(CH₃)₂ | oxalate | 50% | Z/E 90/10 | 142° C. (acetonitrile) | 1600 (C=N); 2500, 2600 (NH+) |
| 6 | H | H | —(CH₂)₃—N(CH₃)₂ | fumarate | 20% | Z/E 60/40 | 130° C. (isopropanol) | 1620 (C=N); 2640 (NH+) |
| 7 | H | H | (CH₂)₂—N(C₂H₅)₂ | fumarate | 40% | Z/E 80/20 | 128° C. (isopropanol) | 1600 (C=N); 2620 (NH+) |
| 8 | H | H | (CH₂)₃—N(C₂H₅)₂ | fumarate | 35% | Z/E 90/10 | 110° C. (acetonitrile/ether) | 1620 (C=N); 2600 (NH+) |
| 9 | H | H | —(CH₂)₂—N(pyrrolidinyl) | oxalate | 60% | Z/E 90/10 | 160° C. (acetonitrile) | 1630 (C=N); 2600 (NH+) |
| 10 | H | H | —(CH₂)₂—N(piperidinyl) | oxalate | 40% | Z/E 90/10 | 189° C. (acetonitrile) | 1620 (C=N); 2660 (NH+) |
| 11 | H | H | —(CH₂)₂—N(piperidinyl) | oxalate | 35% | Z/E 80/20 | 201° C. (acetonitrile) | 1610 (C=N); 2680 (NH+) |
| 12 | H | H | —(CH₂)₂—N(piperidinyl) | oxalate | 55% | Z/E 60/40 | 181° C. (acetonitrile) | 1600 (C=N); 2600 (NH+) |
| 13 | H | H | —CH₂—(N-methylpyrrolidin-2-yl) | oxalate | 50% | Z/E 70/30 | 176° C. (acetonitrile) | 1630 (C=N); 2680 (NH+) |
| 14 | H | CH₃ | —(CH₂)₃—N(CH₃)₂ | fumarate | 70% | Z | 188° C. (acetonitrile) | 1600 (C=N); 2500, 2660 (NH+) |
| 15 | H | CH₃ | —(CH₂)₂—N(CH₂—CH₃)₂ | fumarate | 60% | Z/E 80/20 | 130° C. (acetonitrile) | 1610 (C=N); 2500, 2640 (NH+) |

-continued

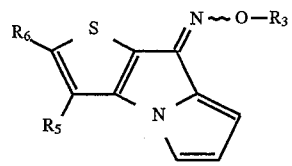

| Ex. | $R_6$ | $R_5$ | $R_3$ | Salt | Yield | Isomer | Melting point | Infrared $\nu$ (cm$^{-1}$) |
|---|---|---|---|---|---|---|---|---|
| 16 | H | $CH_3$ | $-(CH_2)_3-N(C_2H_5)_2$ | fumarate | 60% | Z | 200° C. (acetonitrile) | 1600 (C=N); 2500, 2640 (NH+) |
| 17 | H | $CH_3$ | $-(CH_2)_2-$pyrrolidinyl | oxalate | 52% | Z | 190° C. (acetonitrile) | 1610 (C=N); 2500, 2680 (NH+) |
| 18 | H | $CH_3$ | $-(CH_2)_2-$piperidinyl | oxalate | 50% | Z/E 80/20 | 149° C. (acetonitrile) | 1620 (C=N); 2500, 2660 (NH+) |
| 19 | H | $CH_3$ | $-(CH_2)_2-$piperidinyl | fumarate | 39% | Z | 169° C. (isopropanol) | 1600 (C=N); 2500, 2600 (NH+) |
| 20 | H | $CH_3$ | $-(CH_2)_2-$(N-methyl-pyrrolidin-2-yl) | fumarate | 30% | Z | 190° C. (acetonitrile) | 1630 (C=N); 2500, 2600 (NH+) |
| 21 | H | $CH_3$ | $-CH_2-$(N-methylpiperidin-3-yl) | oxalate | 12% | Z/E 60/40 | 123° C. (isopropanol) | 1620 (C=N); 2500, 2680 (NH+) |
| 22 | H | $CH_3$ | $-CH_2-CH(CH_3)-N(CH_3)_2$ | oxalate | 58% | Z | 166° C. | 1610 (C=N); 2500, 2900 (NH+) |
| 23 | H | $CH_3$ | $-CH_2-CH(CH_3)-CH_2-N(CH_3)_2$ | oxlaate | 65% | Z | 147° C. | 1610 (C=N); 2500, 2690 (NH+) |
| 24 | $4-CH_3O-C_6H_4-$ | H | $-(CH_2)_2-N(CH_3)_2$ | oxalate | 45% | Z/E 80/20 | 201° C. (acetonitrile) | 1600 (C=N); 2500, 2640 (NH+) |
| 25 | $4-CH_3O-C_6H_4-$ | H | $-(CH_2)_3-N(CH_3)_2$ | oxalate | 40% | Z/E 80/20 | 170° C. (acetonitrile) | 1600 (C=N); 2500, 2640 (NH+) |
| 26 | $4-CH_3O-C_6H_4-$ | H | $-(CH_2)_2-$piperidinyl | oxalate | 55% | Z/E 80/20 | 130° C. (acetonitrile) | 1600 (C=N); 2520, 2620 (NH+) |

-continued

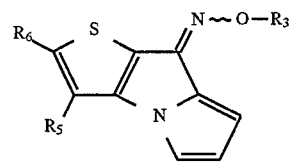

| Ex. | R₆ | R₅ | R₃ | Salt | Yield | Isomer | Melting point | Infrared ν (cm⁻¹) |
|---|---|---|---|---|---|---|---|---|
| 27 | CH₃O—C₆H₄— | H | —CH₂—(N-methylpyrrolidin-2-yl) | oxalate | 35% | Z/E 70/30 | 210° C. (acetonitrile) | 1630 (C=N); 2500, 2600 (NH+) |
| 28 | CH₃—C₆H₄— | H | —(CH₂)₃—N(CH₃)₂ | oxalate | 50% | Z/E 60/40 | 191° C. (acetonitrile) | 1600 (C=N); 2540, 2600 (NH+) |
| 29 | CH₃—C₆H₄— | H | —(CH₂)₂—N(C₂H₅)₂ | oxalate | 15% | Z | 90° C. (acetonitrile/ether) | 1600 (C=N); 2500, 2600 (NH+) |
| 30 | CH₃—C₆H₄— | H | (CH₂)₃—N(C₂H₅)₂ | oxalate | 65% | Z/E 60/40 | 180° C. (acetontrile) | 1600 (C=N); 2500, 2640 (NH+) |
| 31 | CH₃—C₆H₄— | H | —(CH₂)₂—N(piperidino) | oxalate | 45% | Z/E 60/40 | 198° C. (acetonitrile) | 1610 (C=N); 2540, 2700 (NH+) |
| 32 | CH₃—C₆H₄— | H | —(CH₂)₂—N(piperidino) | oxalate | 45% | Z/E 50/50 | 189° C. (acetonitrile) | 1600 (C=N); 2500, 2640 (NH+) |
| 33 | CH₃—C₆H₄— | H | —CH₂—(N-methylpyrrolidin-2-yl) | oxalate | 55% | Z/E 50/50 | 199° C. (acetonitrile) | 1615 (C=N); 2500, 2620 (NH+) |
| 34 | CH₃—C₆H₄— | H | —(CH₂)₂—N(CH₃)₂ | oxalate | 60% | Z/E 60/40 | 212° C. (acetonitrile) | 1600 (C=N); 2540, 2700 (NH+) |
| 35 | H | Cl—C₆H₄— | —(CH₂)₂—N(CH₃)₂ | oxalate | 40% | Z/E 50/50 | 165° C. (ethanol) | 1630 (C=N); 2700, 2640 (NH+) |
| 36 | H | Cl—C₆H₄— | —(CH₂)₃—N(CH₃)₂ | oxalate | 30% | Z/E 50/50 | 180° C. (acetonitrile) | 1620 (C=N); 2700, 2500 (NH+) |
| 37 | H | F—C₆H₄— | —(CH₂)₂—N(CH₃)₂ | oxalate | 48% | Z/E 50/50 | 170° C. (acetonitrile) | 1610 (C=N); 2700, 2500 (NH+) |

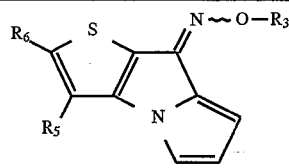

| Ex. | R6 | R5 | R3 | Salt | Yield | Isomer | Melting point | Infrared ν (cm⁻¹) |
|---|---|---|---|---|---|---|---|---|
| 38 | H | Br—⌬— | —(CH₂)₂—N⌬ | oxalate | 50% | Z/E 60/40 | 280° C. (acetonitrile/ isopropanol) | 1620 (C=N); 2700, 2500 (NH+) |

EXAMPLE 39

3-Methyl-8-{[3-(N,N-dimethylamino)-1-phenylprop-1-yloxy]imino}thieno-[2,3-d]pyrrolo[1,2-a]pyrrole

Method A

Add 0.75 g (25 mmol) of sodium hydride to a solution of 1 g (4.89 mmol) of (Z)-3-methyl-8-hydroxyiminothieno[2,3-d]pyrrolo[1,2-a]pyrrole (Preparation 36) in 50 ml of benzene. After the whole has been heated for 1 hour at reflux, add 1.15 g (4.89 mmol) of N,N-dimethyl-3-chloro-3-phenylpropylamine hydrochloride and continue refluxing for 2 hours. After cooling, the precipitate is filtered off and the filtrate is concentrated under reduced pressure and then extracted with diethyl ether. After washing with water and drying, the organic phase is concentrated to dryness to yield the title compound in the form of a base which is then converted into a salt in isopropanol with oxalic acid.

Yield: 6%

Melting point: (oxalate): 210° C. (decomposition)

Infrared: ν cm⁻¹(KBr) (oxalate): 1710 (C=O)

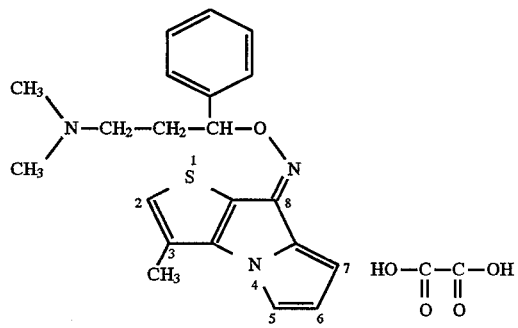

$^1$H NMR: δ(ppm) (DMSO d₆): 2.33 multiplet (5H, CH₂ and CH₃); 2.70 singlet (6H, N(CH₃)₂); 3.00 triplet (2H, CH₂—N); 5.30 multiplet (3H, CH, OH, NH⁺); 6.10 doublet of doublet (1H, H₆); 6.40 doublet of doublet (1H, H₇); 7.30 multiplet (6H, H₉ and C₆H₅); 7.50 singlet (1H, H₂).

Method B

Heat 1 g of (Z)-3-methyl-8-hydroxyiminothieno[2,3-d]pyrrolo[1,2-a]pyrrole, 1.15 g of N,N-dimethyl-3-chloro-3-phenylpropylamine hydrochloride and 0.8 g of sodium hydroxide in 100 ml of methanol at reflux for 26 hours. After cooling and removing the methanol under reduced pressure, the residue is extracted with diethyl ether and then treated as for Method A.

Yield: 15%

EXAMPLE 40

(Z)-3-Methyl-8-[(2-amino-ethoxy)imino]thieno[2,3-d]pyrrolo[1,2-a]pyrrole

Step A: (Z)-3-Methyl-8-[(2-bromo-ethoxy)imino] thieno[2,3-d]pyrrolo[1,2-a]pyrrole Add 5 g of 2-aminoxy-1-bromoethane hydrobromide, 1.5 mol of glacial acetic acid and 1.6 ml of pyridine in succession to a suspension of 1.43 g of 3-methyl-8H-thieno[2,3-d]pyrrolo[1,2-a]pyrrol-2-one (Preparation 29) in 70 ml of ethanol. The reaction mixture is heated at reflux for 3 hours, then the ethanol is removed under reduced pressure and the residue is extracted with 100 ml of diethyl ether. After washing with water, drying, concentrating to dryness and working up again in a diethyl ether/petroleum ether mixture, 1:1, the title compound is obtained in the form of a powder.

Yield: 23%

Melting point: 92° C.

Infrared: ν cm⁻¹(KBr): 2950, 2900, 1490

Step B: (Z)-3-Methyl-8-[(2-phthalimido-ethoxy) imino]thieno[2,3-d]pyrrolo[1,2-a]pyrrole Add 0.98 g of potassium phthalimide to a solution of 1.64 g of (Z)-8-[(2-bromo-ethoxy)imino]thieno[2,3-d]pyrrolo[1,2-a]pyrrole in 30 ml of dimethylformamide, then heat the mixture at reflux for 2 hours. After cooling, the reaction mixture is poured into 200 ml of water and then extracted with 300 ml of ethyl acetate. The organic phase is washed with water, dried over magnesium sulfate, rendered colourless with animal charcoal and then concentrated, and the residue is taken up in a minimum amount of diethyl ether and then filtered and dried.

Yield: 55%

Melting point: 157° C. (acetonitrile/isopropanol, 8:2)

Infrared: ν cm⁻¹(KBr): 1710 (C=O)

Step C: (Z)-3-Methyl-8-[(2-amino-ethoxy)imino] thieno[2,3-d]pyrrolo[1,2-a]pyrrole Add 0.3 ml (6.1 mmol) of hydrazine hydrate to a solution of 0.85 g (2.2 mmol) of (Z)-3-methyl-8-[(2-phthalimido-ethoxy)imino]thieno[2,3-d]pyrrolo[1,2-a]pyrrole in 50 ml of a mixture of ethanol/isopropanol, 1:1. The reaction mixture is heated to reflux. After refluxing the mixture for 30 minutes, add 0.3 ml of hydrazine hydrate and heat at reflux again for 90 minutes. Add 0.5 ml of hydrazine hydrate during the course of the 90 minutes' refluxing. After cooling the reaction mixture, the precipitate formed is removed by filtration and the filtrate is concentrated under reduced pressure. The residue is extracted with diethyl ether and the ethereal phase is washed with water, dried over magnesium sulfate, treated with animal charcoal and concentrated to yield 200 mg of the title product in the form of an oil (base).

Preparation of the oxalate salt

Take up the oil obtained above in 40 ml of isopropanol, then add 90 mg of oxalic acid and heat at reflux for 15 minutes. After cooling, isolate by means of filtration the precipitate that has formed and wash it with isopropanol and then with anhydrous diethyl ether.

Yield: 18%

Melting point (oxalate): 200° C.: decomposition (acetonitrile)

Infrared: ν cm$^{-1}$(KBr): 1720 cm$^{-1}$ (C=O)

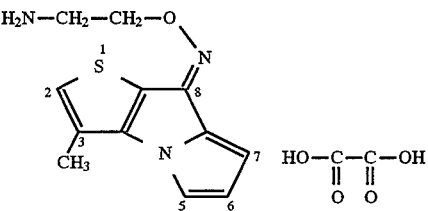

$^1$H NMR: δ(ppm) (DMSO d$_6$): 2.37 singlet (3H, CH$_3$); 3.20 triplet (2H, CH$_2$—N); 4.37 triplet (2H,O—CH$_2$); 6.20 multiplet (5H, H$_6$, NH$_3^+$ and OH); 6.50 doublet of doublet (1H, H$_7$); 7.23 doublet of doublet (1H, H$_9$); 7.50 singlet (1H, H$_2$).

EXAMPLE 41

(Z)-3-Methyl-8-{[2-(N-benzylamino)ethoxy]imino}thieno[2,3-d]pyrrolo[1,2-a]-pyrrole Add 1 g (3.2 mmol) of (Z)-3-methyl-8-[(2-bromo-ethoxy)imino]thieno[2,3-d]pyrrolo[1,2-a]pyrrole, 0.53 g (3.8 mmol) of potassium carbonate and 0.51 g (4.8 mmol) of benzylamine in succession to 20 ml of N,N-dimethylformamide. The reaction mixture is heated at reflux for 3 hours then, after cooling, is poured into 100 ml of water and extracted with diethyl ether. The ethereal phase is washed with water, dried over magnesium sulfate, rendered colourless with animal charcoal and then concentrated under reduced pressure to yield 0.7 g of the title product in the form of an oil (base).

Preparation of the oxalate salt

Take up the oil obtained above in 80 ml of isopropanol, then add 0.2 g of oxalic acid and heat the reaction mixture at reflux for 30 minutes. After cooling, isolate by means of filtration the precipitate that has formed and wash it with isopropanol and then with anhydrous diethyl ether.

Yield: 25%

Melting point (oxalate): 190° C. decomposition (acetonitrile)

Infrared: ν cm$^{-1}$(KBr): 1715 (C=O)

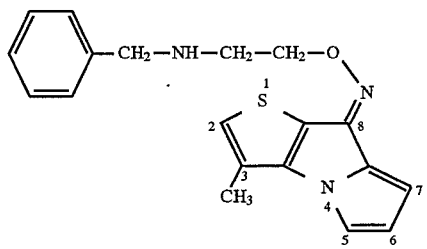

$^1$H NMR: δ(ppm) (DMSO d$_6$): 2.43 singlet (3H, CH$_3$); 3.47 triplet (2H, CH$_2$—NH); 4.30 singlet (2H, CH$_2$—φ); 4.60 triplet (2H, OCH$_2$); 6.27 doublet of doublet (1H, H$_6$); 6.57 doublet of doublet (1H, H$_7$); 6.77 multiplet (3H, NH$_2^+$, OH); 7.30 doublet of doublet (1H, H$_5$); 7.47 multiplet (6H, H$_2$, C$_6$H$_5$).

EXAMPLE 42

(Z)-8-{[2-(N,N-Dimethylamino)ethoxy]imino}thieno[3,2-d]pyrrolo[1,2-a]pyrrole

By proceeding as for Example 3, but replacing the (Z)-8-hydroxyimino-3-methylthieno[2,3-d]pyrrolo[1,2-a]pyrrole with 8-hydroxyiminothieno[3,2-d]pyrrolo[1,2-a]pyrrole (Preparation 53), the title compound is obtained in the form of the oxalate in a yield of 70%.

Melting point (oxalate): >260° C. decomposition (acetonitrile)

Infrared: ν cm$^{-1}$(KBr) (oxalate): 1725 (C=O), 1635 (C=N), 1500, 1090, 960, 900, 835

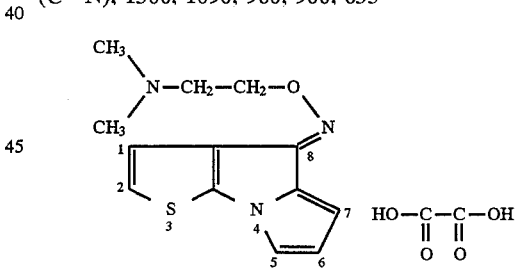

$^1$H NMR: δ(ppm) (DMSO d$_6$): 2.75 singlet (6H, 2×CH$_3$); 3.4 multiplet (2H, CH$_2$); 4.6 multiplet (2H, CH$_2$); 6.12 doublet of doublet (1H, H$_7$); 6.35 doublet of doublet (1H, H$_8$); 7.05 doublet (1H, H$_2$); 7.20 doublet (1H, H$_1$); 7.25 doublet of doublet (1H, H$_6$); 10.4 singlet (1H, OH).

EXAMPLE 43

8-{[2-(N,N-Dimethylamino)ethoxy]imino}-1,2-dimethylthieno[3,2-d]pyrrolo-[1,2-a]pyrrole By proceeding as for Example 42 but using 1,2-dimethyl-8-hydroxyiminothieno[3,2-d]pyrrolo[1,2-a]pyrrole (Preparation 52) as starting material, the title compound is obtained in the form of the oxalate in a yield of: 38%

Melting point (oxalate): 176° C. (acetonitrile)

Infrared: ν cm⁻¹(KBr): 3380, 1710

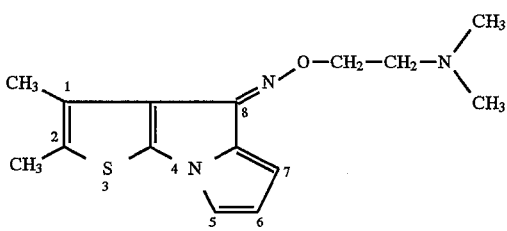

¹H NMR: δ(ppm) (DMSO d₆): 2.13 singlet (3H, CH₃₍₁₎); 2.30 singlet (3H, CH₃₍₂₎); 2.77 singlet (6H, N(CH₃)₂); 3.40 triplet (2H, CH₂N); 4.53 triplet (2H, OCH₂); 6.20 doublet of doublet (1H, H₆); 6.40 multiplet (2H, OH, NH⁺); 7.67 doublet of doublet (1H, H₇); 7.27 doublet of doublet (1H, H₅).

EXAMPLES 44 TO 47

By proceeding as for Example 42, the following are obtained:

EXAMPLE 44

8-[(2-Morpholino-ethoxy)imino]thieno[3,2-d]pyrrolo[1,2-a]pyrrole

EXAMPLE 45

8-{[3-N,N-Dimethylamino)-1-phenyl-n-prop-1-yloxy]imino}thieno[3,2-d]pyrrolo-[1,2-a]pyyrole

EXAMPLE 46

8-[(2-Amino-ethoxy)imino]thieno[3,2-d]pyrrolo[1,2-a]pyrrole

EXAMPLE 47

1,2-Dimethyl 8-[(2-amino-ethoxy)imino]thieno[3,2-d]pyrrolo[1,2-a]pyrrole

EXAMPLE 48

8-[(3-Isopropylamino-2-hydroxy-n-prop-1-yloxy)imino]thieno[3,2-d]pyrrolo [1,2-a]pyrrole The title compound is obtained by proceeding as for Example 1.

EXAMPLE 49

7-Chloro-9-{[2-(N,N-dimethylamino)ethoxy]imino}pyrrolo[1,2-a]indole

Add 5 ml of water, 0.94 g (6.5 mmol) of 1-chloro-2-(N,N-dimethylamino)ethane hydrochloride and 1.19 g (5.44 mmol) of 7-chloro-9-hydroxyiminopyrrolo[1,2-a]indole (Preparation 46) in succession to a solution of 1.56 g (14.7 mmol) of sodium carbonate in 100 ml of acetone, then heat the reaction mixture at reflux for 36 hours. The acetone is removed under reduced pressure and the residue is taken up in 50 ml of water and extracted with diethyl ether. The ethereal phase is washed with water, dried over magnesium sulfate, rendered colourless with animal charcoal, and then concentrated to dryness to yield the title product in the form of an oil (base).

Preparation of the oxalate salt

The oil obtained above is taken up in 50 ml of isopropanol and then 1 equivalent of oxalic acid is added and the mixture is heated for 15 minutes at 40° C. After cooling, the precipitate formed is isolated by filtration and then dried to yield the oxalate salt of the title compound.

Total yield (oxalate): 23%

Melting point (oxalate): 176° C. (acetonitrile)

Infrared: ν cm⁻¹(KBr): 3410 (OH); 3030 (CH); 1710 (C=O)

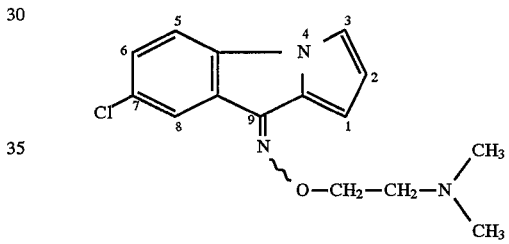

¹H NMR: δ(ppm) (DMSO d6): 2.80 singlet (6H, 2×CH₃); 3.45 multiplet (2H, CH₂—N); 4.62 multiplet (2H, O—CH₂); 6.38 doublet of doublet (1H, H₂); 6.82 doublet of doublet (1H, H₁); 7.55 multiplet (4H, H₃, C₆H₃); 10.28 (m, 2H, CO₂H)

EXAMPLES 50 TO 57

By proceeding in the same manner as for Example 49, but using the appropriate aminohaloalkyl and 9-hydroxyiminopyrrolo[1,2-a]indole, the compounds of the following Examples are obtained:

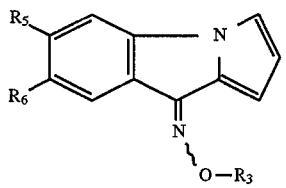

| Ex. | $R_5$ | $R_6$ | $R_3$ | Salt | Yield | Melting point | Infrared | NMR δ (ppm) (DMSO $d_6$) |
|---|---|---|---|---|---|---|---|---|
| 50 | H | Cl | —CH$_2$—CH$_2$—(N-methylpyrrolidinyl) | oxalate, H$_2$O | 37% | 150° C. (sublimation) (acetonitrile) | 3400 (OH); 1610 (C=N) | 2.80(s, 3H); 3.20–2.30–1.90(m, 9H); 4.47(m, 2H); 6.50(m, 5H); 7.50(m, 3H) |
| 51 | H | Cl | —CH$_2$—CH(CH$_3$)—N(CH$_3$)$_2$ | fumarate, H$_2$O | 17% | 138° C. (acetonitrile) | 3420 (OH); 1610 (C=N) | 1.30(m, 3H); 2.50(s, 6H); 2.93–3.38(m, 2H); 4.43(m, 1H); 6.32 (dd, 1H); 6.50(2H); 6.70(dd, 1H); 7.53(m, 4H) |
| 52 | H | CH$_3$ | —CH$_2$—CH(CH$_3$)—N(CH$_3$)$_2$ | oxalate | 12% | 135° C. (acetonitrile) | 3410 (OH); 1600 (C=N) | 1.35(d, 3H); 2.35(s, 3H); 2.80 (s, 6H); 3.80–3.37(m, 1H); 4.87–4.53(m, 2H); 6.03(m, 2H); 6.37 (dd, H$_2$); 6.77(dd, 1H); 7.53–7.43–7.30(m, 4H) |
| 53 | H | CH$_3$ | —CH$_2$—CH$_2$—(N-methylpyrrolidinyl) | oxalate | 40% | 190° C. (acetonitrile) | 3410 (OH); 1615 (C=N) | 2.03(m, 6H); 2.35(s, 3H); 2.78 (s, 3H); 3.25(m, 4H); 4.61(m, 1H); 6.21(m, 2H); 6.33(dd, 1H); 6.63(dd, 1H); 7.38–7.23(m, 4H) |
| 54 | H | H | —CH$_2$—CH$_2$—N(CH$_3$)$_2$ | oxalate | 27% | 183° C. (acetonitrile) | 3430 (OH); 1610 (C=N) | 2.80(s, 6H); 3.43(t, 2H); 4.60(t, 2H); 6.33(dd, 1H); 6.75(dd, 1H); 7.63–7.15(m, 5H) |
| 55 | H | H | —CH$_2$—CH(CH$_3$)—N(CH$_3$)$_2$ | oxalate | 41% | 142° C. (acetonitrile) | 3400 (OH); 1610 (C=N) | 1.37(d, 3H); 2.78(s, 6H); 3.75–3.55(m, 1H); 4.55(m, 2H); 6.42 (m, 2H); 6.78–6.37(m, 2H); 7.58–7.15(m, 5H) |
| 56 | H | H | —CH$_2$—CH$_2$—(N-methylpyrrolidinyl) | oxalate | 28% | 157° C. (acetonitrile) | 3410 (OH); 1620 (C=N) | 3.28–1.90(m, 10H); 3.53(t, 2H); 4.17(m, 2H); 6.55(m); 6.33(dd, 1H); 6.73(dd, 1H); 7.53–7.10(m, 5H) |
| 57 | Cl | H | —CH$_2$—CH(CH$_3$)—N(CH$_3$)$_2$ | 0.5 oxalate, H$_2$O | 46% | 160° C. (acetonitrile) | 3420 (OH); 1600 (C=N) | 1.33(d, 3H); 2.77(s, 6H); 3.73–3.27(m, 1H); 4.53(m, 2H); 6.40 (dd, 1H); 6.78(dd, 1H); 7.23(m, 3H); 7.63–7.53(m, 2H); 7.77(d, 1H) |

EXAMPLE 58

6-Chloro-9-{[3-(N,N-dimethylamino)-1-phenyl-n-prop-1-yloxy]imino}pyrrolo-[1,2-a]indole By proceeding as for Example 39, but replacing the (Z)-3-methyl-8-hydroxyiminothieno[2,3-d]pyrrolo-[1,2-a] pyrrole with 6-chloro-9-hydroxyiminopyrrolo[1,2-a]indole, the title compound is obtained, the oxalate salt of which is prepared in a total yield of 23%.

Melting point (oxalate): 120° C. decomposition
Infrared: ν cm⁻¹(KBr): 1705 (C=O)

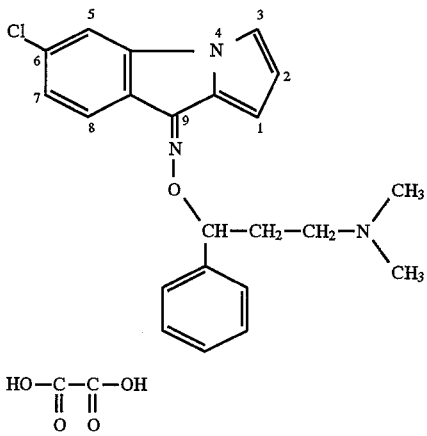

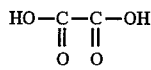

¹H NMR: δ(ppm) (DMSO d₆): 2.50 triplet (2H, CH₂—N); 2.73 singlet (6H, N(CH₃)₂); 3.13 quadruplet (2H, CH₂); 5.07 multiplet (2H, OH, NH⁺); 5.40 multiplet (1H, CH); 6.43 doublet of doublet (1H, H₂); 7.87 doublet of doublet (1H, H₁); 7.60-7.33 multiplet (8H, C₆H₃ and C₆H₅); 7.77 doublet of doublet (1H, H₃)

EXAMPLE 59

9-[(2-Amino-ethoxy)imino]pyrrolo[1,2-a]indole

Step A: 9-[(2-Bromo-ethoxy)imino]pyrrolo[1,2-a]indole

By proceeding as for Step A of Example 40, but replacing the 3-methyl-8H-thieno[3,2-b]pyrrolo[2,1-e]pyrrol-2-one with pyrrolo[1,2-a]indol-9-one, 9-[(2-bromo-ethoxy)imino]pyrrolo[1,2-a]indole is obtained in a yield of 89%.

Melting point: 65° C.

Step B: 9-[(2-Phthalimido-ethoxy)imino]pyrrolo[1,2-a]indole

By proceeding as for Step B of Example 40, but replacing the (Z)-3-methyl-8-[(2-bromo-ethoxy)imino]-thieno[3,2-b]pyrrolo[2,1-e]pyrrole with 9-[(2-bromo-ethoxy)imino]pyrrolo[1,2-a]indole, 9-[(2-phthalimido-ethoxy)imino]pyrrolo[1,2-a]indole is obtained in a yield of 55%.

Melting point: 195° C.

Step C: 9-[(2-Amino-ethoxy)imino]pyrrolo[1,2-a]indole

By proceeding as for Step C of Example 40, but replacing the (Z)-3-methyl-8-[(2-phthalimido-ethoxy)-imino]thieno[3,2-b]pyrrolo[2,1-e]pyrrole with 9-[(2-phthalimido-ethoxy)imino]pyrrolo[1,2-a]indole, the title compound, of which the oxalate salt is then prepared, is obtained.

Total yield (oxalate): 48%

Melting point (oxalate): 165° C. decomposition (acetonitrile)

Infrared: ν cm⁻¹(KBr): 3280, 3090, 2940, 1710, 1620

EXAMPLE 60

9-{[2-(N-Benzylamino)ethoxy]imino}pyrrolo[1,2-a]indole

By proceeding as for Example 41, the title compound is obtained in the form of a base, and then, after conversion into a salt with oxalic acid, in the form of the oxalate.

Total yield (oxalate): 16%

Melting point (oxalate): 230° C. decomposition (acetonitrile)

Infrared: ν cm⁻¹(KBr): 3200, 2830, 1710, 1620, 1480

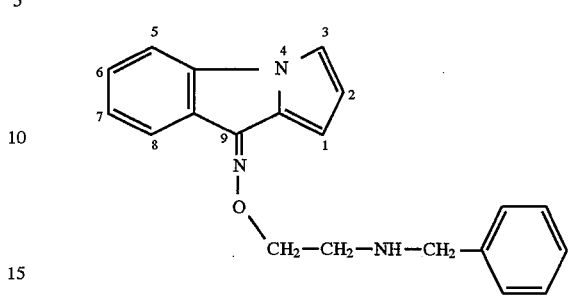

¹H NMR: δ(ppm) (DMSO d₆): 3.33 multiplet (2H, CH₂NH); 4.20 singlet (2H, CH₂-φ); 4.57 multiplet (2H, CH₂O); 6.33 doublet of doublet (1H, H₂); 6.77 doublet of doublet (1H, H₁); 7.06 multiplet (2H, NH⁺, OH); 7.40 multiplet (10H, C₆H₅, H₃, H₅, H₆, H₇, H₈).

EXAMPLES 61 TO 63

By proceeding as for Example 59, the following are obtained:

EXAMPLE 61

6-Chloro-9-[(2-amino-ethoxy)imino]pyrrolo[1,2-a]indole

EXAMPLE 62

7-Chloro-9-[(2-amino-ethoxy)imino]pyrrolo[1,2-a]indole

EXAMPLE 63

7-Methyl-9-[(2-amino-ethoxy)imino]pyrrolo[1,2-a]indole

EXAMPLES 64 TO 67

By proceeding as for Example 49, the following are obtained:

EXAMPLE 64

9-[(2-Morpholino-ethoxy)imino]pyrrolo[1,2-a]indole

EXAMPLE 65

9-[(2-Piperidino-ethoxy)imino]pyrrolo[1,2-a]indole

EXAMPLE 66

7-Chloro-9-{[2-(N,N-diethylamino)ethoxy]imino}pyrrolo[1,2-a]indole

EXAMPLE 67

7-Methyl-9-{[3-(N,N-dimethylamino)-2-methyl-n-prop-1-yloxy]imino}pyrrolo[1,2-a]indole

EXAMPLES 68 AND 69

By proceeding as for Example 1, the following are obtained:

EXAMPLE 68

9-[(3-Isopropylamino-2-hydroxy-n-prop-1-yloxy)imino]pyrrolo[1,2-a]indole

EXAMPLE 69

7-Methyl-9-[(3-isopropylamino-2-hydroxy-n-prop-1-yloxy)imino]pyrrolo[1,2-a]indole

EXAMPLES 70 TO 72

By proceeding as for Examples 41 and 39, the following are obtained:

EXAMPLE 70

8-{[2-(N-Indan-2-ylamino)ethoxy]imino}thieno[2,3-d]pyrrolo[1,2-a]pyrrole

EXAMPLE 71

3-Methyl-8-{[3-(N-indan-2-ylamino)-1-phenylprop-1-yloxy]imino}thieno[2,3-d]-pyrrolo[1,2-a]pyrrole

EXAMPLE 72

8-{[2-(N-Methyl-N-(3-trifluoromethyl)phenylprop-2-yl)ethoxy]imino}-3-methylthieno[2,3-d]pyrrolo[1,2-a]pyrrole

EXAMPLES 73 TO 80

By proceeding as for Example 49, the following are obtained:

EXAMPLE 73

9-{[2-(N-Benzylamino)-n-prop-1-yloxy]imino}pyrrolo[1,2-a]indole

EXAMPLE 74

9-{[2-(N-Benzylamino)-2-isobutyl-ethoxy]imino}pyrrolo[1,2-a]indole

EXAMPLE 75

9-{[2-(N-Benzylamino)-2-phenylethoxy]imino}pyrrolo[1,2-a]indole

EXAMPLE 76

9-{[2-(N-Benzyl-N-methylamino)-2-phenylethoxy]imino}pyrrolo[1,2-a]indole

EXAMPLE 77

9-{[2-(N-Phenylamino)-2-isobutylethoxy]imino}pyrrolo[1,2-a]indole

EXAMPLE 78

9-{[2-(N-Phenethylamino)-n-prop-1-yloxy]imino}pyrrolo[1,2-a]indole

EXAMPLE 79

9-{[2-(N-Methylamino)-2-phenethyl]imino}pyrrolo[1,2-a]indole

EXAMPLE 80

9-{[2-(N-Indan-2-ylamino)ethoxy]imino}pyrrolo[1,2-a]indole

PHARMACOLOGICAL STUDY OF THE COMPOUNDS OF THE INVENTION

EXAMPLE A

Study of the Receptor Binding of the Compounds of the Invention

A-1: Study of the binding of the compounds of the invention to 5-$HT_3$ serotoninergic receptors The binding of the compounds of the invention to 5-$HT_3$ receptors was determined for each compound by measuring the displacement of $^3$H-zacopride (specific ligand for 5-$HT_3$ receptors) in rat area postrema homogenates.

PROTOCOL

Aliquot amounts (50–100 µl) of a membrane suspension (2.5–5.0 mg of protein/$cm^3$) are incubated for 30 minutes at 25° C. in a Tris-HCl buffer, 25 mM, pH 7.4, in the presence of 0.3–0.4 nM $3^H$-zacopride (83 ci/mmol) (total volume: 0.5 $cm^3$). The incubation is terminated by filtering the samples through Whatman GF/B filters which are then washed and dried. The radioactivity retained on the filters is finally calculated by spectrometry in liquid medium (Aquasol). The non-specific binding is evaluated under the same conditions using samples containing in addition 1 µM of ondansetron (5-$HT_3$ antagonist). The displacement curves obtained by adding increasing concentrations of a test compound to the incubation medium are analysed to determine the affinity of the test compounds for 5-$HT_3$ receptors.

A-2: Study of the binding of the compounds of the invention to the serotonin reuptake site as well as to 5-$HT_1$, 5-$HT_{1A}$, 5-$HT_{1B}$, 5-$HT_{1D}$, 5-$HT_2$, 5-$HT_{2C}$, 5-$HT_4$ serotoninergic receptors.

The binding of the compounds of the invention is measured in accordance with conventional methods.

for the serotonin reuptake site, by the displacement of $^3$H-paroxetine in rat brain from which the cerebellum has been removed, for 5-$HT_1$ receptors, by the displacement of 5-OH tryptamine in pig frontal cortex and striatum, for 5-$HT_{1A}$ receptors, by the displacement of 8-OH-DPAT in rat hippocampus homogenates, for 5-$HT_{1B}$ receptors, by the displacement of 5-hydroxytryptamine in rat cortex, striatum, and globus pallidus homogenates, for 5-$HT_{1D}$ receptors, by the displacement of 5-OH-tryptamine in rat cortex, striatum and globus pallidus homogenates, for 5-$HT_2$ receptors, by the displacement of aminoiodoketaneserine in rat frontal cortex homogenates, for 5-$HT_{2C}$ receptors, by the displacement of N-methylmesulergine in rat frontal cortex and hippocampus homogenates, for 5-$HT_4$ receptors, by the displacement of GR 113808 in guinea pig striatum or hippocampus.

CONCLUSION

The compounds of the invention appear to possess a very strong affinity for 5-HT$_3$ and/or 5HT$_{2C}$ serotoninergic receptors as well as for serotonin reuptake sites. That strong affinity is doubled by a high selectivity in relation to other serotoninergic receptors. The IC$_{50}$ values obtained for the compounds of the invention are compiled in the following Table (I):

TABLE (I)

IC$_{50}$ values obtained for serotonin reuptake sites and serotoninergic receptors

| Ex. | Serotonin reuptake sites | 5-HT$_1$ | 5-HT$_{1A}$ | 5-HT$_{1B}$ | 5-HT$_{1D}$ | 5-HT$_2$ | 5-HT$_{2C}$ | 5-HT$_3$ |
|---|---|---|---|---|---|---|---|---|
| 3  | $1.2 \times 10^{-7}$ | $2.2 \times 10^{-6}$ | $5.8 \times 10^{-6}$ | $2.7 \times 10^{-6}$ | $4.8 \times 10^{-7}$ | $3.1 \times 10^{-6}$ | $2.1 \times 10^{-6}$ | $1.1 \times 10^{-10}$ |
| 4  | $8.9 \times 10^{-7}$ | $5.5 \times 10^{-7}$ | $4.8 \times 10^{-7}$ | $6.1 \times 10^{-7}$ | $4.1 \times 10^{-7}$ | $5.0 \times 10^{-6}$ | $8.2 \times 10^{-7}$ | $3.5 \times 10^{-9}$ |
| 13 | $6.0 \times 10^{-7}$ | $1.6 \times 10^{-5}$ | $>10^{-4}$ | $3.1 \times 10^{-5}$ | $1.1 \times 10^{-5}$ | $1.4 \times 10^{-5}$ | $1.0 \times 10^{-6}$ | $2.0 \times 10^{-9}$ |
| 14 | $1.1 \times 10^{-6}$ | $1.1 \times 10^{-5}$ | $2.2 \times 10^{-5}$ | $3.2 \times 10^{-5}$ | $7.0 \times 10^{-6}$ | $4.2 \times 10^{-5}$ | $1.8 \times 10^{-5}$ | $2.5 \times 10^{-9}$ |
| 15 | $1.3 \times 10^{-7}$ | $1.1 \times 10^{-5}$ | $2.1 \times 10^{-5}$ | $6.4 \times 10^{-6}$ | $4.0 \times 10^{-6}$ | $1.3 \times 10^{-5}$ | $8.4 \times 10^{-7}$ | $5.0 \times 10^{-9}$ |
| 17 | $3.0 \times 10^{-7}$ | $3.0 \times 10^{-6}$ | $1.6 \times 10^{-6}$ | $3.6 \times 10^{-6}$ | $3.2 \times 10^{-6}$ | $3.7 \times 10^{-6}$ | $7.1 \times 10^{-7}$ | $2.0 \times 10^{-9}$ |
| 18 | $2.6 \times 10^{-7}$ | $5.1 \times 10^{-6}$ | $5.7 \times 10^{-6}$ | $1.4 \times 10^{-5}$ | $7.5 \times 10^{-6}$ | $5.2 \times 10^{-6}$ | $1.2 \times 10^{-6}$ | $4.0 \times 10^{-9}$ |
| 22 | $1.1 \times 10^{-7}$ | $6.9 \times 10^{-6}$ | $9.0 \times 10^{-6}$ | $1.1 \times 10^{-5}$ | $6.4 \times 10^{-6}$ | $1.1 \times 10^{-5}$ | $1.6 \times 10^{-6}$ | $1.0 \times 10^{-9}$ |
| 23 | $5.0 \times 10^{-6}$ | $9.6 \times 10^{-6}$ | $5.2 \times 10^{-5}$ | $2.4 \times 10^{-5}$ | $1.1 \times 10^{-5}$ | $1.4 \times 10^{-5}$ | $2.0 \times 10^{-6}$ | $5.4 \times 10^{-9}$ |
| 39 | $7.2 \times 10^{-8}$ | $1.0 \times 10^{-5}$ | $1.1 \times 10^{-5}$ | $>10^{-4}$ | $6.7 \times 10^{-6}$ | $2.2 \times 10^{-6}$ | $6.1 \times 10^{-8}$ | $2.0 \times 10^{-7}$ |
| 40 | $5.8 \times 10^{-7}$ | $9.0 \times 10^{-7}$ | $3.1 \times 10^{-6}$ | $9.2 \times 10^{-7}$ | $2.7 \times 10^{-6}$ | $1.5 \times 10^{-5}$ | $1.8 \times 10^{-7}$ | $2.4 \times 10^{-8}$ |
| 41 | $1.1 \times 10^{-7}$ | $2.7 \times 10^{-6}$ | $9.2 \times 10^{-6}$ | $4.4 \times 10^{-6}$ | $1.1 \times 10^{-5}$ | $4.1 \times 10^{-6}$ | $4.13 \times 10^{-7}$ | $2.9 \times 10^{-8}$ |
| 49 | $1.2 \times 10^{-5}$ | $2.4 \times 10^{-6}$ | $2.1 \times 10^{-5}$ | $1.4 \times 10^{-6}$ | $3.1 \times 10^{-6}$ | $7.6 \times 10^{-6}$ | $1.1 \times 10^{-5}$ | $8.6 \times 10^{-8}$ |
| 52 | $1.3 \times 10^{-5}$ | $2.0 \times 10^{-6}$ | $3.3 \times 10^{-6}$ | $3.8 \times 10^{-6}$ | $8.1 \times 10^{-7}$ | $8.4 \times 10^{-6}$ | $2.3 \times 10^{-6}$ | $4.4 \times 10^{-8}$ |
| 53 | $2.4 \times 10^{-5}$ | $8.3 \times 10^{-6}$ | $1.4 \times 10^{-5}$ | $3.5 \times 10^{-5}$ | $5.5 \times 10^{-6}$ | $2.2 \times 10^{-6}$ | $6.0 \times 10^{-6}$ | $3.7 \times 10^{-8}$ |
| 54 | $9.3 \times 10^{-7}$ | $1.4 \times 10^{-7}$ | $1.1 \times 10^{-6}$ | $1.1 \times 10^{-6}$ | $6.9 \times 10^{-7}$ | $1.4 \times 10^{-5}$ | $1.4 \times 10^{-6}$ | $5.7 \times 10^{-9}$ |
| 55 | $3.2 \times 10^{-7}$ | $2.8 \times 10^{-6}$ | $3.8 \times 10^{-6}$ | $4.4 \times 10^{-6}$ | $1.4 \times 10^{-6}$ | $1.2 \times 10^{-5}$ | $4.1 \times 10^{-6}$ | $5.3 \times 10^{-9}$ |

EXAMPLE B

Anxiolytic Activity Study—Illuminated/Darkened Cages Test on the Mouse

The anxiolytic effects of the compounds of the invention were studied in accordance with the illuminated/darkened cages test on the mouse (Crawley et al. (1981), Pharmacol. Biochem. Behav., 15, pp 695–699).

PROTOCOL

The test uses two cages of equal size (20×20×14 cm) made of PVC. One is strongly illuminated by a 100 W bulb ("cold" light) and the other is darkened. The two cages are separated from one another by a small opaque tunnel (5×7 cm). The mice are introduced individually into the tunnel and, once they have entered the darkened cage for the first time, a recording is made over a period of 5 minutes, by means of pads connected to a computer, of the time spent by the animals in the illuminated cage as well as the number of transfers between the darkened cage and the illuminated cage. Each experimental group comprises a minimum of 15 animals.

RESULTS

By comparison with the control, the compounds of the invention, administered by the intraperitoneal route, cause an increase in the time spent by the mouse in the illuminated cage as well as an increase in the number of transfers between the darkened cage and the illuminated cage. That significant increase of the two parameters studied demonstrates the prominent anxiolytic activity of the compounds of the invention.

TABLE II

Study of the anxiolytic activity
(Illuminated/darkened cages test)
(Results given as a percentage compared with the control group)

| Example 22 | Dose: 15 mg/kg, i.p. route |
|---|---|
| Time spent in the illuminated cage | +92%* |
| Number of transfers | +76%* |

*$p < 0.5$

EXAMPLE C

Antidepressant Activity Study—Forced Swimming Test on the Mouse

The antidepressant effects of the compounds of the invention were studied in accordance with the forced swimming test on the mouse. (Behavioural despair in mice: a primary screening test for antidepressants, Porsolt R. D. et al, Arch. Int. Pharmacodyn., (1977), 229, pp. 327–336).

PROTOCOL

The animals are placed for 6 minutes in a cylinder containing water from which they cannot escape. The period of immobility of the animals is measured for the last 4 minutes of the test. The test compounds are administered in a single dose before the test (imipramine being used as the reference compound).

RESULTS

The immobility of the mouse in the water reflects a depressive state as a result of the situation in which it finds itself (aversion situation which it cannot change). Compared with the controls, the compounds of the invention reduce very significantly the period of immobility of the animals which, in this test, is indicative of antidepressant properties.

TABLE III

Study of the antidepressant activity
(Forced swimming test)
(Period of immobility expressed as a percentage by comparison with the control group)

| | Dose (mg/kg, i.p. route) | |
|---|---|---|
| Example | 32 | 64 |
| 3 | −39%* | −86%*** |
| 39 | −53%** | — |

*$p < 0.5$
**$p < 0.01$
***$p < 0.001$

EXAMPLE D

Tablets each Comprising 5 mg of (Z)-3-Methyl-8-{[2-(N,N-Dimethyl-Amino)Ethoxy]Imino}Thieno[3,2-b]Pyrrolo[1,2-a]Pyrrole Oxalate Formulation for the preparation of 1000 tablets

| | |
|---|---|
| (Z)-3-methyl 8-{[2-(N,N-dimethylamino)ethoxy]imino}-thieno[2,3-d]pyrrolo[1,2-a]pyrrole oxalate | 5 g |
| Corn starch | 70 g |
| Wheat starch | 70 g |
| Lactose | 300 g |
| Magnesium stearate | 1 g |
| Silica | 1 g |
| Hydroxypropyl cellulose | 2 g |

We claim:

1. A compound selected from those of formula (I):

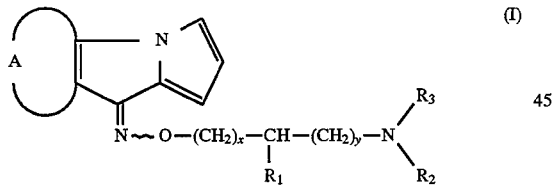

wherein $R_1$ is selected from:
hydrogen,
alkyl,
alkenyl,
cycloalkyl,
cycloalkyl in which the alkyl chain is straight or branched and has 1 to 4 carbon atoms inclusive,
hydroxy,
alkoxy,
unsubstituted or substituted phenyl,
unsubstituted of substituted phenylalkyl in which the alkyl chain is straight or branched and has 1 to 4 carbon atoms inclusive,
unsubstituted or substituted phenoxy, and
unsubstituted or substituted phenylalkoxy in which the alkyl chain is straight or branched and has 1 to 4 carbon atoms inclusive, or $R_1$ forms with $R_2$ and the chain

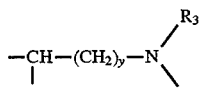

carrying them
a nitrogen-containing ring system having 5 to 8 ring members inclusive, $R_2$ and $R_3$ are each selected, independently of the other, from:
hydrogen,
alkyl,
alkenyl,
cycloalkyl,
unsubstituted or substituted indanyl,
cycloalkylalkyl in which the alkyl chain is straight or branched and has 1 to 4 carbon atoms inclusive,
unsubstituted or substituted phenyl, and
unsubstituted or substituted phenylalkyl in which the alkyl chain is straight or branched and has 1 to 4 carbon atoms inclusive, or $R_2$ and $R_3$ form together with the nitrogen atom carrying them a heterocyclic system selected from:

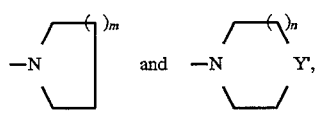

wherein:
m is 0, 1, 2, 3, or 4,
n is 0, 1, or 2,
Y' is selected from oxygen, sulfur and

$R_4$ being selected from:
hydrogen,
alkyl, and
unsubstituted or substituted —$(CH_2)_\sigma$-phenyl, wherein $\sigma$ is 0, 1, 2, 3, or 4, x and y are identical or different and are 0, 1, 2, 3, or 4, A represents:
a group of formula (α):

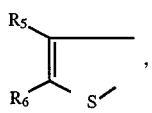

and thus forms with the heterocyclic system carrying it a thieno[2,3-d]pyrrolo[1,2-a]pyrrole of the formula ($I_\alpha$):

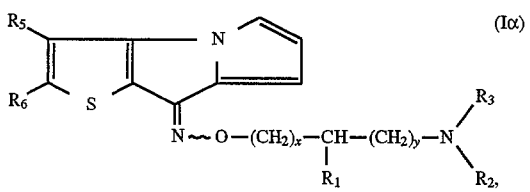

wherein R₁, R₂, R₃, x, and y are as defined hereinbefore and R₅ and R₆, which are identical or different, each represents, independently of the other, a group selected from:
hydrogen,
alkyl,
hydroxy,
alkoxy,
halogen,
trifluoromethyl,
alkoxycarbonyl,
unsubstituted or substituted —(CH₂)ₚ-phenyl wherein p is 0, 1, 2, 3, or 4, and
unsubstituted or substituted —O—(CH₂)ₚ'-phenyl wherein p' is 0, 1, 2, 3, or 4,
a group of formula (β):

and thus forms with the heterocyclic system carrying it a thieno[3,2-d]pyrrolo[1,2-a]pyrrole of the formula (I_β):

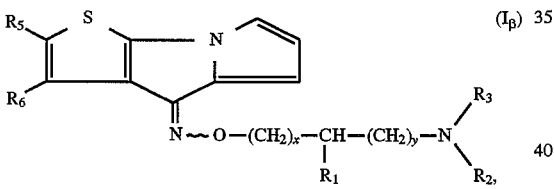

wherein R₁, R₂, R₃, R₅, R₆, x and y are as defined hereinbefore,
a group of formula (γ):

and thus forms with the heterocyclic system carrying it a pyrrolo[1,2-a]indole of the formula (Iγ):

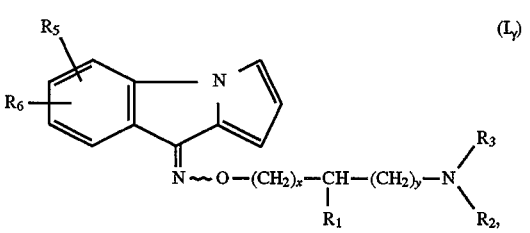

wherein R₁, R₂, R₃, R₅, R₆, x and y are as defined hereinbefore,
their cis or trans isomers in respect of the oxime ether, their enantiomers or diastereoisomers, and
their hydrates and/or pharmaceutically-acceptable addition salts with an acid or a base,
it being understood, unless specified otherwise, that:
the terms "alkyl" and "alkoxy" represent a straight-chain or branched group having 1 to 6 carbon atoms inclusive,
the term "alkenyl" represents a straight-chain or branched unsaturated group having 2 to 6 carbon atoms inclusive,
the term "cycloalkyl" represents a carbon ring system having 3 to 8 ring members inclusive,
the expressions "substituted indanyl", "substituted phenyl", "substituted phenoxy", "substituted phenylalkyl", "substituted —(CH₂)α-phenyl", "substituted —(CH₂)ₚ-phenyl", substituted "—O—(CH₂)ₚ'-phenyl" and "substituted phenylalkoxy" denote that the phenyl radical is substituted by one or more identical or different substituents selected from alkyl, alkoxy, hydroxy, halogen, trifluoromethyl, nitrile and nitro.

2. A compound according to claim 1 wherein A represents a group of formula (α):

and thus forms with the heterocyclic system carrying it a thieno[2,3-d]pyrrolo[1,2-a]pyrrole of the formula (I_α):

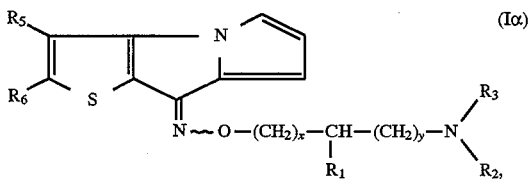

wherein R₁, R₂, R₃, x, and y are as defined in claim 1 and R₅ and R₆, which are identical or different, each represents, independently of the other, a group selected from:
hydrogen,
alkyl,
hydroxy,
alkoxy,
halogen,
trifluoromethyl,
alkoxycarbonyl,
unsubstituted or substituted —(CH₂)ₚ-phenyl wherein p is 0, 1, 2, 3, or 4, and
unsubstituted or substituted —O—(CH₂)ₚ'-phenyl wherein p' is 0, 1, 2, 3, or 4,
their cis or trans isomers in respect of the oxime ether, their enantiomers or diastereoisomers, and
their hydrates and/or pharmaceutically-acceptable addition salts with an acid or a base,
it being understood, unless specified otherwise, that:
the terms "alkyl" and "alkoxy" represent straight-chain or branched groups having 1 to 6 carbon atoms inclusive,
the expressions "substituted —(CH₂)ₚ-phenyl" and "substituted —O—(CH₂)ₚ'-phenyl" denote that the phenyl radical is substituted by one or more identical or different substituents selected from alkyl, alkoxy, hydroxy, halogen, trifluoromethyl, nitrile and nitro.

3. A compound according to claim 1 wherein A represents a group of formula (β):

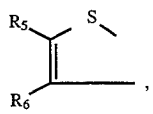

and thus forms with the heterocyclic system carrying it a thieno[3,2-d]pyrrolo[1,2-a]pyrrole of the formula (I$_\beta$):

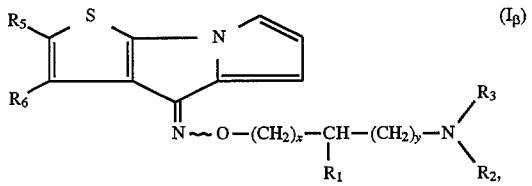

wherein R$_1$, R$_2$, R$_3$, x and y are as defined in claim 1 and R$_5$ and R$_6$, which are identical or different, each represents, independently of the other, a group selected from:
  hydrogen,
  alkyl,
  hydroxy,
  alkoxy,
  halogen,
  trifluoromethyl,
  alkoxycarbonyl,
  unsubstituted or substituted —(CH$_2$)$_p$-phenyl wherein p is 0, 1, 2, 3, or 4, and
  unsubstituted or substituted —O—(CH$_2$)$_{p'}$-phenyl wherein p' is 0, 1, 2, 3, or 4, their cis or trans isomers in respect of the oxime ether, their enantiomers or diastereoisomers, and their hydrates and/or pharmaceutically-acceptable addition salts with an acid or a base, it being understood, unless specified otherwise, that:

the terms "alkyl" and "alkoxy" represent straight-chain or branched groups having 1 to 6 carbon atoms inclusive, the expressions "substituted —(CH$_2$)$_p$-phenyl" and "substituted —O—(CH$_2$)$_{p'}$-phenyl" denote that the phenyl radical is substituted by one or more identical or different substituents selected from alkyl, alkoxy, hydroxy, halogen, trifluoromethyl, nitrile and nitro.

4. A compound according to claim 1 wherein A represents a group of formula (γ):

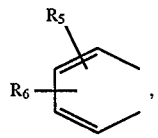

and forms with the heterocyclic system carrying it a pyrrolo [1,2-a]indole of the formula (I$\gamma$):

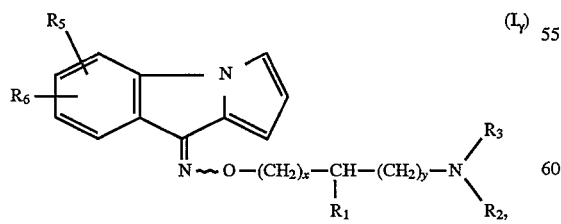

wherein R$_1$, R$_2$, R$_3$, x, and y are as defined in claim 1 and R$_5$ and R$_6$, which are identical or different, each represents, independently of the other, a group selected from:
  hydrogen,
  alkyl,
  hydroxy,
  alkoxy,
  halogen,
  trifluoromethyl,
  alkoxycarbonyl,
  unsubstituted or substituted —(CH$_2$)$_p$-phenyl wherein p is 0, 1, 2, 3, or 4, and
  unsubstituted or substituted —O—(CH$_2$)$_{p'}$-phenyl wherein p' is 0, 1, 2, 3, or 4, their cis or trans isomers in respect of the oxime ether, their enantiomers or diastereoisomers, and their hydrates and/or pharmaceutically-acceptable addition salts with an acid or a base, it being understood, unless specified otherwise, that:

the terms "alkyl" and "alkoxy" represent straight-chain or branched groups having 1 to 6 carbon atoms inclusive, the expressions "substituted —(CH$_2$)$_p$-phenyl" and "substituted —O—(CH$_2$)$_{p'}$-phenyl" denote that the phenyl radical is substituted by one or more identical or different substituents selected from alkyl, alkoxy, hydroxy, halogen, trifluoromethyl, nitrile and nitro.

5. A compound according to claim 1, which is selected from 3-methyl-8-{[3-(N,N-dimethylamino)-1-phenyl-n-prop-1-yloxy]imino}thieno[2,3-d]pyrrolo[1,2-a]pyrrole for which the formula is shown below, and its Z and E isomers and its enantiomers, isolated or in the form of a mixture, and its pharmaceutically-acceptable addition salts with an acid

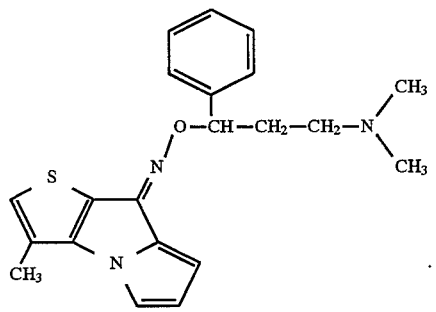

6. A compound according to claim 1 which is selected from 3-methyl-8-{[2-(N-benzylamino)ethoxy]imino}thieno[2,3-d]pyrrolo[1,2-a]pyrrole for which the formula is shown below, and its Z and E isomers, isolated or in the form of a mixture, and its pharmaceutically-acceptable addition salts with an acid

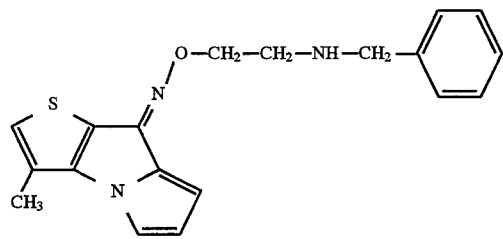

7. A compound according to claim 1, which is selected from 3-methyl-8-{[2-(N,N-dimethylamino)-n-prop-1-yloxy]imino}thieno[2,3-d]pyrrolo[1,2-a]pyrrole for which the formula is shown below, and its Z and E isomers and its enantiomers, isolated or in the form of a mixture, and its pharmaceutically-acceptable addition salts with an acid

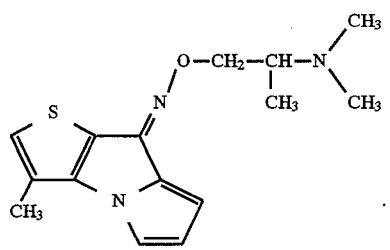

8. A compound according to claim 1, which is selected from 8-{[2-(N,N-dimethylamino)ethoxy]imino}thieno[3,2-d]pyrrolo[1,2-a]pyrrole for which the formula is shown below, and its Z and E isomers, isolated or in the form of a mixture, and its pharmaceutically-acceptable addition salts with an acid

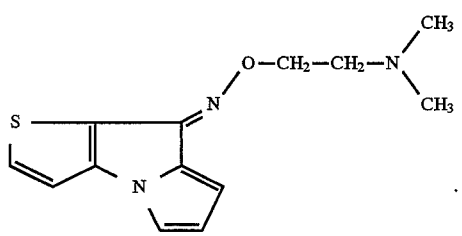

9. A compound according to claim 1, which is selected from 9-{[2-(N,N-dimethylamino)-n-prop-1-yloxy]imino}pyrrolo[1,2-a]indole for which the formula is shown below, and its Z and E isomers and its enantiomers, isolated or in the form of a mixture, and its pharmaceutically-acceptable addition salts with an acid

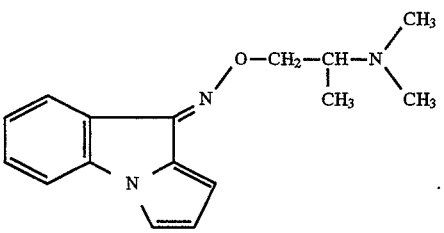

10. A method for treating a mammal afflicted with a disease requiring a selective seratonin reuptake site and $5\text{-HT}_{2c}$ and/or $5\text{-HT}_3$ ligand comprising the step of administering to said mammal an amount of a compound of claim 1 which is effective for alleviation of said disease.

11. A pharmaceutical composition useful as a $5\text{-HT}_{2c}$ and/or $5\text{-HT}_3$ ligand provider comprising an effective amount of a compound as claimed in claim 1, together with a pharmaceutically-acceptable excipient.

* * * * *

UNITED STATES PATENT AND TRADEMARK OFFICE
CERTIFICATE OF CORRECTION

PATENT NO.   : 5,627,203
DATED        : May 20, 1997
INVENTOR(S)  : Sylvain Rault et al.

It is certified that error appears in the above-indentified patent and that said Letters Patent is hereby corrected as shown below:

Column 9, line 46:  Remove the comma "," between " invention and very".

Column 17, line 58:  "wetter" should read -- water --.

Column 25, line 51:  "1Isoproylamino" should read -- Isopropylamino --.

Column 31:  Example number 27 and 33, under the "$R_3$" column "-$CH_2$-" should read -- -$(CH_2)_2$- --.

Column 47, line 24:  Delete "{" at the end of the line.

Column 47, line 25:  Insert -- { -- at the beginning of the line.

Column 47, line 61:  "of" should read -- or --.

Signed and Sealed this

Fifth Day of August, 1997

*Attest:*

BRUCE LEHMAN

*Attesting Officer*   Commissioner of Patents and Trademarks